(12) United States Patent
Harshman et al.

(10) Patent No.: US 10,973,559 B2
(45) Date of Patent: *Apr. 13, 2021

(54) SYSTEMS AND METHODS FOR INTERMEDULLARY BONE FIXATION

(71) Applicants: University of British Columbia, Vancouver (CA); British Columbia Cancer Agency Branch, Vancouver (CA)

(72) Inventors: Edward Scott Harshman, Woodinville, WA (US); Steven Charles Dimmer, Bellevue, WA (US); David Thomas Stinson, Woodinville, WA (US)

(73) Assignees: University of British Columbia, Vancouver (CA); British Columbia Cancer Agency Branch, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/384,758

(22) Filed: Apr. 15, 2019

(65) Prior Publication Data
US 2019/0231401 A1 Aug. 1, 2019

Related U.S. Application Data

(63) Continuation of application No. 15/519,148, filed as application No. PCT/US2015/055441 on Oct. 14, 2015, now Pat. No. 10,258,394.
(Continued)

(51) Int. Cl.
*A61B 17/72* (2006.01)
*A61B 17/00* (2006.01)

(52) U.S. Cl.
CPC ...... *A61B 17/7283* (2013.01); *A61B 17/7225* (2013.01); *A61B 17/7233* (2013.01); *A61B 17/7266* (2013.01); *A61B 2017/00477* (2013.01)

(58) Field of Classification Search
CPC ............. A61B 17/72–7291; A61B 17/74–748
See application file for complete search history.

(56) References Cited

U.S. PATENT DOCUMENTS

| 4,706,659 | A | * | 11/1987 | Matthews | ............ | A61B 17/164 |
| | | | | | | 464/173 |
| 5,108,397 | A | | 4/1992 | White | | |
| | | | (Continued) | | | |

FOREIGN PATENT DOCUMENTS

| AT | 509852 B | 12/2011 |
| CN | 2699846 | 5/2005 |
| | (Continued) | |

OTHER PUBLICATIONS

European Patent Office, "Communication pursuant to Article 94(3) from EP Application No. 15850096.7", from Foreign Counterpart to U.S. Appl. No. 15/519,148, dated Oct. 15, 2019, pp. 1-5, Published: EP.
(Continued)

*Primary Examiner* — Eduardo C Robert
*Assistant Examiner* — Michelle C Eckman
(74) *Attorney, Agent, or Firm* — Fogg & Powers LLC

(57) ABSTRACT

Systems and methods for intermedullary bone fracture fixation are described herein. The fixation device includes a main body having a flexible state and a rigid state. The fixation device further includes a proximal interface coupled to a proximal end of the main body to anchor the fixation device to an exterior surface of the bone and a distal interface coupled to a distal end of the main body to anchor
(Continued)

the fixation device to an interior cavity of the bone. The fixation device further includes a locking interface to configured to convert the main body from the flexible state to the rigid state.

20 Claims, 15 Drawing Sheets

Related U.S. Application Data

(60) Provisional application No. 62/063,526, filed on Oct. 14, 2014.

(56) References Cited

U.S. PATENT DOCUMENTS

| | | | |
|---|---|---|---|
| 5,167,665 A | 12/1992 | Mckinney | |
| 5,234,435 A | 8/1993 | Seagrave, Jr. | |
| D346,218 S | 4/1994 | White | |
| 5,300,071 A | 4/1994 | Browner et al. | |
| 5,336,224 A | 8/1994 | Selman | |
| 5,527,309 A | 6/1996 | Shelton | |
| 5,527,310 A | 6/1996 | Cole et al. | |
| 5,593,407 A | 1/1997 | Reis | |
| 5,601,550 A | 2/1997 | Esser | |
| 5,649,925 A * | 7/1997 | Barbera Alacreu | A61B 17/7013 606/103 |
| 5,879,352 A * | 3/1999 | Filoso | A61B 17/7013 606/60 |
| 5,944,719 A | 8/1999 | Leban | |
| 6,340,362 B1 | 1/2002 | Pierer et al. | |
| 6,368,326 B1 | 4/2002 | Dakin et al. | |
| 7,258,692 B2 * | 8/2007 | Thelen | A61B 17/1668 606/62 |
| 7,410,483 B2 * | 8/2008 | Danitz | A61B 1/0055 606/1 |
| 7,625,395 B2 | 12/2009 | Muckter et al. | |
| 7,632,277 B2 | 12/2009 | Woll et al. | |
| 7,785,325 B1 * | 8/2010 | Milbank | A61B 17/7208 606/62 |
| 7,846,162 B2 | 12/2010 | Nelson et al. | |
| 8,043,347 B2 | 10/2011 | Jiang et al. | |
| 8,128,626 B2 | 3/2012 | Justin | |
| 8,128,627 B2 | 3/2012 | Justin et al. | |
| 8,206,389 B2 | 6/2012 | Huebner et al. | |
| 8,372,074 B2 | 2/2013 | Milbank | |
| 8,409,257 B2 | 4/2013 | Edidin et al. | |
| 8,439,916 B2 | 5/2013 | Coati et al. | |
| 8,632,543 B2 | 1/2014 | Metzinger et al. | |
| 8,961,516 B2 * | 2/2015 | Nelson | A61B 17/7208 606/64 |
| 9,060,809 B2 * | 6/2015 | Tipirneni | A61B 17/683 |
| 9,144,506 B2 * | 9/2015 | Phelps | A61F 2/4455 |
| 9,155,574 B2 * | 10/2015 | Saravia | A61B 17/7208 |
| 9,482,260 B1 * | 11/2016 | Krause | A61B 17/8625 |
| 9,498,264 B2 | 11/2016 | Harshman et al. | |
| 9,839,435 B2 | 12/2017 | Meek et al. | |
| 2002/0032444 A1 | 3/2002 | Mische | |
| 2002/0087161 A1 | 7/2002 | Randall et al. | |
| 2002/0198527 A1 | 12/2002 | Muckter | |
| 2003/0078582 A1 | 4/2003 | Heggeness | |
| 2003/0181982 A1 | 9/2003 | Kuslich | |
| 2003/0187449 A1 * | 10/2003 | McCleary | A61B 17/1668 606/80 |
| 2004/0024409 A1 | 2/2004 | Sand et al. | |
| 2004/0102778 A1 | 5/2004 | Huebner et al. | |
| 2004/0215191 A1 | 10/2004 | Kitchen | |
| 2005/0055023 A1 * | 3/2005 | Sohngen | A61B 17/7241 606/62 |
| 2005/0085819 A1 | 4/2005 | Ellis et al. | |
| 2005/0154390 A1 | 7/2005 | Biedermann et al. | |
| 2005/0165401 A1 | 7/2005 | Pack | |
| 2006/0074421 A1 | 4/2006 | Bickley et al. | |
| 2006/0264950 A1 | 11/2006 | Nelson et al. | |
| 2007/0083204 A1 | 4/2007 | Sidebotham | |
| 2007/0162132 A1 | 7/2007 | Messerli | |
| 2007/0233111 A1 | 10/2007 | Orbay et al. | |
| 2008/0051786 A1 | 2/2008 | Jensen | |
| 2008/0058722 A1 | 3/2008 | Von Oepen et al. | |
| 2008/0077133 A1 | 3/2008 | Schulze | |
| 2008/0077154 A1 | 3/2008 | Edwards et al. | |
| 2008/0108989 A1 | 5/2008 | Parsell et al. | |
| 2008/0161805 A1 * | 7/2008 | Saravia | A61B 17/8872 606/60 |
| 2008/0195145 A1 | 8/2008 | Bonutti et al. | |
| 2008/0234676 A1 | 9/2008 | Schulze et al. | |
| 2008/0249628 A1 | 10/2008 | Altarac et al. | |
| 2008/0269745 A1 * | 10/2008 | Justin | A61B 17/864 606/62 |
| 2008/0287951 A1 * | 11/2008 | Stoneburner | A61B 17/7208 606/63 |
| 2008/0294163 A1 * | 11/2008 | Chou | A61B 17/7291 606/62 |
| 2008/0294164 A1 | 11/2008 | Frank et al. | |
| 2009/0024174 A1 | 1/2009 | Stark | |
| 2009/0048672 A1 | 2/2009 | Essenmacher | |
| 2009/0062797 A1 | 3/2009 | Huebner et al. | |
| 2009/0192512 A1 | 7/2009 | Sommers | |
| 2009/0216232 A1 | 8/2009 | Buford, III et al. | |
| 2010/0023010 A1 * | 1/2010 | Nelson | A61B 17/7208 606/62 |
| 2010/0076503 A1 | 3/2010 | Beyar et al. | |
| 2010/0185290 A1 | 7/2010 | Compton et al. | |
| 2010/0217333 A1 | 8/2010 | McShane et al. | |
| 2010/0249832 A1 | 9/2010 | Stopek et al. | |
| 2010/0249838 A1 | 9/2010 | Stopek et al. | |
| 2010/0249854 A1 | 9/2010 | Thomas et al. | |
| 2010/0249944 A1 | 9/2010 | Thomas et al. | |
| 2010/0262239 A1 | 10/2010 | Boyden et al. | |
| 2010/0286692 A1 | 11/2010 | Greenhalgh et al. | |
| 2010/0298893 A1 | 11/2010 | Stucki | |
| 2010/0318137 A1 | 12/2010 | Stucki et al. | |
| 2010/0331842 A1 * | 12/2010 | Milbank | A61B 17/6416 606/62 |
| 2011/0015684 A1 | 1/2011 | Belcheva et al. | |
| 2011/0028974 A1 | 2/2011 | Chemello | |
| 2011/0040282 A1 | 2/2011 | Uihlein | |
| 2011/0046746 A1 | 2/2011 | Rabiner et al. | |
| 2011/0087227 A1 * | 4/2011 | Mazur | A61B 17/7208 606/62 |
| 2011/0098757 A1 | 4/2011 | Schelling | |
| 2011/0098816 A1 | 4/2011 | Jacob et al. | |
| 2011/0098817 A1 | 4/2011 | Eckhardt et al. | |
| 2011/0119815 A1 | 5/2011 | Paulson et al. | |
| 2011/0144643 A1 | 6/2011 | Lorenz et al. | |
| 2011/0144645 A1 | 6/2011 | Saravia et al. | |
| 2011/0144703 A1 * | 6/2011 | Krause | A61B 17/8625 606/309 |
| 2011/0153454 A1 | 6/2011 | Dunn et al. | |
| 2011/0184518 A1 | 7/2011 | Trieu | |
| 2011/0184519 A1 | 7/2011 | Trieu | |
| 2011/0184520 A1 | 7/2011 | Trieu | |
| 2011/0196435 A1 | 8/2011 | Forsell | |
| 2011/0230966 A1 | 9/2011 | Trieu | |
| 2011/0238181 A1 | 9/2011 | Trieu | |
| 2011/0264229 A1 | 10/2011 | Donner | |
| 2011/0288598 A1 | 11/2011 | Moed et al. | |
| 2011/0306975 A1 | 12/2011 | Kaikkonen et al. | |
| 2011/0319944 A1 | 12/2011 | Borodic | |
| 2012/0010617 A1 | 1/2012 | Maza | |
| 2012/0078252 A1 | 3/2012 | Huebner et al. | |
| 2012/0078311 A1 | 3/2012 | Huebner et al. | |
| 2012/0083847 A1 | 4/2012 | Huebner et al. | |
| 2012/0083895 A1 | 4/2012 | Conway et al. | |
| 2012/0101533 A1 | 4/2012 | Purcell et al. | |
| 2012/0101576 A1 | 4/2012 | Dewey et al. | |
| 2013/0006145 A1 | 1/2013 | Toomey et al. | |
| 2013/0006245 A1 | 1/2013 | Stoneburner et al. | |
| 2013/0012942 A1 * | 1/2013 | Nelson | A61B 17/7266 606/63 |
| 2013/0131678 A1 | 5/2013 | Dahners | |

(56) References Cited

U.S. PATENT DOCUMENTS

| | | | |
|---|---|---|---|
| 2013/0144348 | A1 | 6/2013 | Schwappach |
| 2013/0325007 | A1 | 12/2013 | Beyar et al. |
| 2014/0114312 | A1* | 4/2014 | Krause .............. A61B 17/866 606/62 |
| 2014/0309636 | A1 | 10/2014 | Meek et al. |
| 2014/0358146 | A1 | 12/2014 | Meek et al. |
| 2015/0157370 | A1* | 6/2015 | Gross .............. A61M 31/002 604/506 |
| 2015/0257800 | A1* | 9/2015 | Harshman .......... A61B 17/1717 606/62 |
| 2017/0014170 | A1* | 1/2017 | Fallin .............. A61B 17/7291 |
| 2017/0020585 | A1 | 1/2017 | Harshman et al. |
| 2017/0238977 | A1* | 8/2017 | Harshman .......... A61B 17/7225 |
| 2019/0282280 | A1 | 9/2019 | Harshman et al. |
| 2020/0054372 | A1 | 2/2020 | Stinson et al. |

FOREIGN PATENT DOCUMENTS

| | | |
|---|---|---|
| CN | 101633119 A | 1/2010 |
| CN | 101636119 A | 1/2010 |
| CN | 102793579 A | 11/2012 |
| CN | 104203132 A | 12/2014 |
| CN | 104203132 B | 8/2017 |
| CN | 107106217 A | 8/2017 |
| EP | 2779928 A1 | 9/2014 |
| EP | 3326558 A1 | 5/2018 |
| EP | 3206608 | 7/2018 |
| WO | 2007009123 A2 | 1/2007 |
| WO | 2008116175 A2 | 9/2008 |
| WO | 2008120877 A1 | 10/2008 |
| WO | 2009143374 A2 | 11/2009 |
| WO | 2010124230 A1 | 10/2010 |
| WO | 2011067668 A1 | 6/2011 |
| WO | 2011119815 A2 | 9/2011 |
| WO | 2011153454 A2 | 12/2011 |
| WO | 2012107913 A2 | 8/2012 |
| WO | 2013063145 A1 | 5/2013 |
| WO | 2013071432 A1 | 5/2013 |
| WO | 2015134750 A1 | 9/2015 |
| WO | 2016061173 A1 | 4/2016 |
| WO | 2018067888 A1 | 4/2018 |
| WO | 2020077457 A1 | 4/2020 |

OTHER PUBLICATIONS

U.S. Patent and Trademark Office, "Restriction Requirement", U.S. Appl. No. 15/952,093, dated Nov. 29, 2019, pp. 1-8, Published: US.

Canadian Intellectual Property Office, "Notice of Allowance from CA Application No. 2964370", from Foreign Counterpart to U.S. Appl. No. 15/519,148, dated Dec. 13, 2019, p. 1, Published: CA.

"UT Southwest Medical Surgeons Market Pelvic Fracture Device," accessed at http://www.texasbusiness.com/ut-southwest-medical-surgeons-market-pelvic-fracture-device-cms-4418, Apr. 22, 2011, pp. 1-5, Texas Business.com.

Australian Government IP Australia, "Examination report No. 1 for standard patent application from AU Application No. 2015333623 dated Sep. 26, 2017", from Foreign Counterpart to U.S. Appl. No. 15/519,148, dated Sep. 26, 2017, pp. 1-4, Published: AU.

Australian Government IP Australia, "Notice of acceptance for patent application from AU Application No. 2015333623 dated Jul. 20, 2018", from Foreign Counterpart to PCT Application No. PCT/US2015/055441, dated Jul. 20, 2018, pp. 1-3, Published: AU.

Australian Government IP Australia, "Notice of Acceptance from AU Application No. 2012339536 dated Jan. 28, 2016", from Foreign Counterpart to PCT Application No. PCT/CA2012/050808, dated Jan. 28, 2016, pp. 1-3, Published: AU.

Australian Government IP Australia, "Patent Examination Report No. 1 from AU Application No. 2012339536 dated Jan. 23, 2015", from Foreign Counterpart to U.S. Appl. No. 14/357,917, dated Jan. 23, 2015, pp. 1-5, Published: AU.

Australian Government IP Australia, "Patent Examination Report No. 2 from AU Application No. 2012339536 dated Oct. 16, 2015", from Foreign Counterpart to U.S. Appl. No. 14/357,917, dated Oct. 16, 2015, pp. 1-6, Published: AU.

Barry et al., "Flexible intramedullary nails for fractures in children", Aspects of Current Management, Sep. 2004, pp. 1-7, vol. 86-B, No. 7, British Editorial Society of Bone and Joint Surgery.

Canadian Intellectual Property Office, "Office Action from CA Application No. 2,855,752 dated Feb. 3, 2017", from Foreign Counterpart to U.S. Appl. No. 14/357,917, dated Feb. 3, 2017, pp. 1-4, Published: CA.

Canadian Intellectual Property Office, "Office Action from CA Application No. 2,855,752 dated Mar. 9, 2018", from Foreign Counterpart to U.S. Appl. No. 14/357,917, dated Mar. 9, 2018, pp. 1-5, Published: CA.

Canadian Intellectual Property Office, "Office Action from CA Application No. 2,855,752 dated Oct. 28, 2015", from Foreign Counterpart to U.S. Appl. No. 14/357,917, dated Oct. 28, 2015, pp. 1-4, Published: CA.

Canadian Intellectual Property Office, "Office Action from CA Application No. 2,964,370 dated Jan. 24, 2019", from Foreign Counterpart to U.S. Appl. No. 15/519,148, dated Jan. 24, 2019, pp. 1-6, Published: CA.

Canadian Intellectual Property Office, "Office Action from CA Application No. 2,964,370 dated May 4, 2018", from Foreign Counterpart to U.S. Appl. No. 15/519,148, dated May 4, 2018, pp. 1-7, Published: CA.

Canadian Intellectual Property Office, "Office Action from CA Application No. 2978697 dated Oct. 19, 2018", from Foreign Counterpart to PCT Application No. PCT/US2015/018969, dated Oct. 19, 2018, pp. 1-4, Published: CA.

Cheung, et al., "A new halo-pelvic apparatus", Spine, (2003), vol. 28, No. 3, pp. 1-8.

China National Intellectual Property Office, "Office Action from CN Application No. 201580061380.2 dated Dec. 21, 2018", from Foreign Counterpart to U.S. Appl. No. 15/519,148, dated Dec. 21, 2018, pp. 1-18, Published: CN.

European Patent Office, "Communication pursuant to Article 94(3) from EP Application No. 12849005.9 dated Jun. 2, 2016", from Foreign Counterpart to U.S. Appl. No. 14/357,917, dated Jun. 2, 2016, pp. 1-4, Published: EP.

European Patent Office, "Communication pursuant to Article 94(3) from EP Application No. 12849005.9 dated Nov. 25, 2016", from Foreign Counterpart to PCT Application No. PCT/CA2012/050808, dated Nov. 25, 2016, pp. 1-4, Published: EP.

European Patent Office, "Communication under Rule 71(3) from EP Application No. 12849005.9 dated Jul. 25, 2017", from Foreign Counterpart to U.S. Appl. No. 14/357,917, dated Jul. 25, 2017, pp. 1-6, Published: EP.

European Patent Office, "Extended European Search Report from EP Application No. 12849005.9 dated Jun. 15, 2015", from Foreign Counterpart to PCT Application No. PCT/CA2012/050808, dated Jun. 15, 2015, pp. 1-6, Published: EP.

European Patent Office, "Extended European Search Report from EP Application No. 15850096.7 dated Jun. 8, 2018", from Foreign Counterpart to U.S. Appl. No. 15/519,148, dated Jun. 8, 2018, pp. 1-12, Published: EP.

European Patent Office, "Extended European Search Report from EP Application No. 17207050.0 dated Apr. 20, 2018", from Foreign Counterpart to U.S. Appl. No. 14/357,917, dated Apr. 20, 2018, pp. 1-6, Published: EP.

Ganz, et al., "Surgical dislocation of the adult hip", the Journal of Bone and Joint Surgery (BR), Nov. 2004, pp. 1119-1124, vol. 83-B, No. 8, British Editorial Society of Bone and Joint Surgery.

Griffin et al., "Vertically Unstable Pelvic Fractures Fixed with Percutaneous Iliosacral Screws: Does Posterior Injury Pattern Prediction Fixation Failure?", Journal of Orthopedic Trauma, Jan. 2006, pp. 399-405, vol. 17, No. 6, Lippincott Williams, and Wilkins, Inc.

International Bureau, "International Preliminary Report on Patentability from PCT Application No. PCT/CA2012/050808 dated May 20, 2014", from Foreign Counterpart to U.S. Appl. No. 14/357,917, dated May 20, 2014, pp. 1-6, Published: Switzerland.

(56) References Cited

OTHER PUBLICATIONS

International Searching Authority, "International Search Report and Written Opinion from PCT Application No. PCT/CA2012/050808 dated Feb. 26, 2013", from Foreign Counterpart to U.S. Appl. No. 14/357,917, dated Feb. 26, 2013, pp. 1-10, Published: WO.
International Searching Authority, "International Search Report and Written Opinion from PCT Application No. PCT/US2015/055441 dated Feb. 9, 2016", from Foreign Counterpart to U.S. Appl. No. 15/519,148, dated Feb. 9, 2016, pp. 1-15, Published: WO.
International Searching Authority, "International Search Report and Written Opinion from PCT Application No. PCT/US2017/055442 dated Dec. 11, 2017", dated Dec. 11, 2017, pp. 1-14, Published: US.
International Searching Authority, "International Search Report and Written Opinion of the International Searching Authority from PCT Application No. PCT/US15/18969 dated May 27, 2015", from Foreign Counterpart to U.S. Appl. No. 14/727,576, dated May 27, 2015, pp. 1-6, Published: US.
Japanese Patent Office, "Decision to Grant from JP Application No. 2017519539 dated Jul. 31, 2018", from Foreign Counterpart to PCT Application No. PCT/US2015/055441, dated Jul. 31, 2018, pp. 1-3, Published: JP.
Japanese Patent Office, "Office Action from JP Application No. 2017519539 dated Jan. 10, 2018", from Foreign Counterpart to PCT Application No. PCT/US2015/055441, dated Jan. 10, 2018, pp. 1-6, Published: JP.
Miller et al., "Variations in Sacral Morphology and Implications for Iliosacral Screw Fixation", Journal of the American Academy of Orthopaedic Surgeons, Jan. 2012, pp. 8-16, vol. 20, No. 1, American Academy of Orthopaedic Surgeons.
Novick, "Pelvic Fractures/Acetabular Fractures", Hospital for Special Surgery, Mar. 30, 2006, pp. 1-9, HSS.edu.
Novick, "Pelvic Fractures/Fractures of the Acetabulum", Hospital for Special Surgery, Mar. 30, 2006, pp. 1-10.
Starr et al., "Superior Pubic Ramus Fractures Fixed With Percutaneous Screws: What Predicts Fixation Failure?", Journal of Orthopaedic Trauma, Feb. 2008, pp. 81-87, vol. 22, No. 2, Lippincott Williams and Wilkins.
Starr, "Fractures of the Pelvic Ring," in Rockwood & Green's Fractures in Adults fith Edition, Chapter-41, accessed on Feb. 4, 2014, pp. 1-40, Lippincott Williams & Wilkins.
State Intellectual Property Office of P.R. China, "Notification on Grant of the Patent Right for Invention from CN Application No. 2012800661802 dated Apr. 28, 2017", from Foreign Counterpart to PCT Application No. PCT/CA2012/050808, dated Apr. 28, 2017, pp. 1-3, Published: CN.
State Intellectual Property Office, P.R. China, "Office Action from CN Application No. 201280066180.2 dated Aug. 3, 2016", from Foreign Counterpart to U.S. Appl. No. 14/357,917, dated Aug. 3, 2016, pp. 1-6, Published: CN.
State Intellectual Property Office, P.R. China, "Office Action from CN Application No. 201280066180.2 dated Dec. 28, 2015", from Foreign Counterpart to U.S. Appl. No. 14/357,917, dated Dec. 28, 2015, pp. 1-7, Published: CN.
State Intellectual Property Office, P.R. China, "Search Report from CN Application No. 201280066180.2 dated Aug. 10, 2016", from Foreign Counterpart to U.S. Appl. No. 14/357,917, dated Aug. 10, 2016, pp. 1-3, Published: CN.
State Intellectual Property Office, P.R. China, "Third Office Action from CN Application No. 201280066180.2 dated Jan. 5, 2017", from Foreign Counterpart to U.S. Appl. No. 14/357,917, dated Jan. 5, 2017, pp. 1-4, Published: CN.
U.S. Patent and Trademark Office, "Advisory Action", U.S. Appl. No. 14/300,752, dated Feb. 16, 2017, pp. 1-3, Published: US.
U.S. Patent and Trademark Office, "Advisory Action", U.S. Appl. No. 14/300,752, dated Oct. 7, 2015, pp. 1-3, Published: US.
U.S. Patent and Trademark Office, "Final Office Action", U.S. Appl. No. 14/300,752, dated Jan. 12, 2018, pp. 1-37, Published: US.
U.S. Patent and Trademark Office, "Final Office Action", U.S. Appl. No. 14/300,752, dated May 28, 2015, pp. 1-14, Published: US.
U.S. Patent and Trademark Office, "Final Office Action", U.S. Appl. No. 14/300,752, dated Nov. 3, 2016, pp. 1-15, Published: US.
U.S. Patent and Trademark Office, "Final Office Action", U.S. Appl. No. 14/357,917, dated Sep. 6, 2016, pp. 1-11, Published: US.
U.S. Patent and Trademark Office, "Interview Summary" U.S. Appl. No. 14/727,576, dated Feb. 17, 2016, pp. 14, Published: US.
U.S. Patent and Trademark Office, "Interview Summary", U.S. Appl. No. 14/727,576, dated Jun. 14, 2016, pp. 1-3, Published: US.
U.S. Patent and Trademark Office, "Notice of Allowance" U.S. Appl. No. 14/727,576, dated Jul. 19, 2016, pp. 1-8, Published: US.
U.S. Patent and Trademark Office, "Notice of Allowance", U.S. Appl. No. 14/357,917, dated Jul. 26, 2017, pp. 1-5, Published: US.
European Patent Office, "Extended European Search Report from EP Application No. 17859233.3", from Foreign Counterpart to U.S. Appl. No. 16/340,067, dated Apr. 23, 2020, pp. 1 through 8, Published: EP.
Canadian Intellectual Property Office, "Office Action from CA Application No. 2855752 dated Jun. 17, 2019", from Foreign Counterpart to U.S. Appl. No. 14/357,917, pp. 1-3, Published: CA.
China National Intellectual Property Administration, "Notice of Decision of Granting Patent Right for Invention from CN Application No. 201580061380.2 dated Sep. 10, 2019", from Foreign Counterpart to U.S. Appl. No. 15/519,148, pp. 1-5, Published: CN.
European Patent Office, "Communication pursuant to Article 94(3) from EP Application No. 17207050.0 dated Jul. 22, 2019", from Foreign Counterpart to U.S. Appl. No. 14/357,917, pp. 1-5, Published: EP.
International Bureau, "International Preliminary Report on Patentability from PCT Application No. PCT/US2017/055442 dated Apr. 18, 2019", from Foreign Counterpart to U.S. Appl. No. 16/340,067, pp. 1-8, Published: WO.
U.S. Patent and Trademark Office, "Notice of Allowance", U.S. Appl. No. 15/285,811, dated Mar. 25, 2019, pp. 1-11, Published: US.
U.S. Patent and Trademark Office, "Notice of Allowance", U.S. Appl. No. 15/519,148, dated Feb. 13, 2019, pp. 1-42, Published: US.
U.S. Patent and Trademark Office, "Office Action for U.S. Appl. No. 15/285,811 dated Oct. 18, 2018", pp. 1-39, Published in: US.
U.S. Patent and Trademark Office, "Office Action", U.S. Appl. No. 14/300,752, dated Apr. 5, 2016, pp. 1-16, Published: US.
U.S. Patent and Trademark Office, "Office Action", U.S. Appl. No. 14/300,752, dated Aug. 8, 2017, pp. 1-16, Published: US.
U.S. Patent and Trademark Office, "Office Action", U.S. Appl. No. 14/300,752, dated Oct. 20, 2014, pp. 1-14, Published: US.
U.S. Patent and Trademark Office, "Office Action", U.S. Appl. No. 14/357,917, dated Apr. 18, 2016, pp. 1-10, Published: US.
U.S. Patent and Trademark Office, "Office Action", U.S. Appl. No. 14/727,576, dated Oct. 16, 2015, pp. 1-14, Published: US.
U.S. Patent and Trademark Office, "Office Action", U.S. Appl. No. 14/727,576, dated Apr. 28, 2016, pp. 1-15, Published: US.
U.S. Patent and Trademark Office, "Office Action", U.S. Appl. No. 15/519,148, dated Jul. 26, 2018, pp. 1-38, Published: US.
U.S. Patent and Trademark Office, "Restriction Requirement", U.S. Appl. No. 14/357,917, dated Jan. 21, 2016, pp. 1-6, Published: US.
U.S. Patent and Trademark Office, "Restriction Requirement", U.S. Appl. No. 14/727,576, dated Jul. 23, 2015. pp. 1-10, Published: US.
U.S. Patent and Trademark Office, "Restriction Requirement", U.S. Appl. No. 15/285,811, dated Mar. 30, 2018, pp. 1-7, Published: US. US 7,273,482, (withdrawn).
Vaidya, R., et al., "Complications of Anterior Subcutaneous Internal Fixation for Unstable Pelvis Fractures: A Multicenter Study," Clinical Orthopaedicsand Related Research, Aug. 2012, pp. 1-8 vol. 470, No. 8, Springer.
U.S. Patent and Trademark Office, "Office Action", U.S. Appl. No. 15/952,093, dated Mar. 6, 2020, pp. 1-71, Published: US.
International Searching Authority, "International Search Report and Written Opinion from PCT Application No. PCT/CA2019/051471", dated Feb. 5, 2020, pp. 1-14, Published: WO.
U.S. Patent and Trademark Office, "Office Action", U.S. Appl. No. 16/414,435, dated Jul. 14, 2020, pp. 1 through 62, Published: US.
U.S. Patent and Trademark Office, "Final Office Action", U.S. Appl. No. 15/952,093, dated Sep. 25, 2020, pp. 1 through 19, Published: US.

(56) References Cited

OTHER PUBLICATIONS

European Patent Office, "Communication pursuant to Article 94(3) EPC from EP Application No. 17207050.0", from Foreign Counterpart to U.S. Appl. No. 14/357,917, dated Aug. 26, 2020, pp. 1 through 3, Published: EP.

European Patent Office, "Communication pursuant to Article 94(3) EPC from EP Application No. 15850096.7", from Foreign Counterpart to U.S. Appl. No. 15/519,148, dated Sep. 21, 2020, pp. 1 through 4, Published: EP.

U.S. Patent and Trademark Office, "Restriction Requirement", U.S. Appl. No. 16/340,067, dated Dec. 16, 2020, pp. 1 through 7, Published: US.

U.S. Patent and Trademark Office, "Advisory Action", U.S. Appl. No. 15/952,093, dated Jan. 13, 2021, pp. 1 through 6, Published: US.

\* cited by examiner

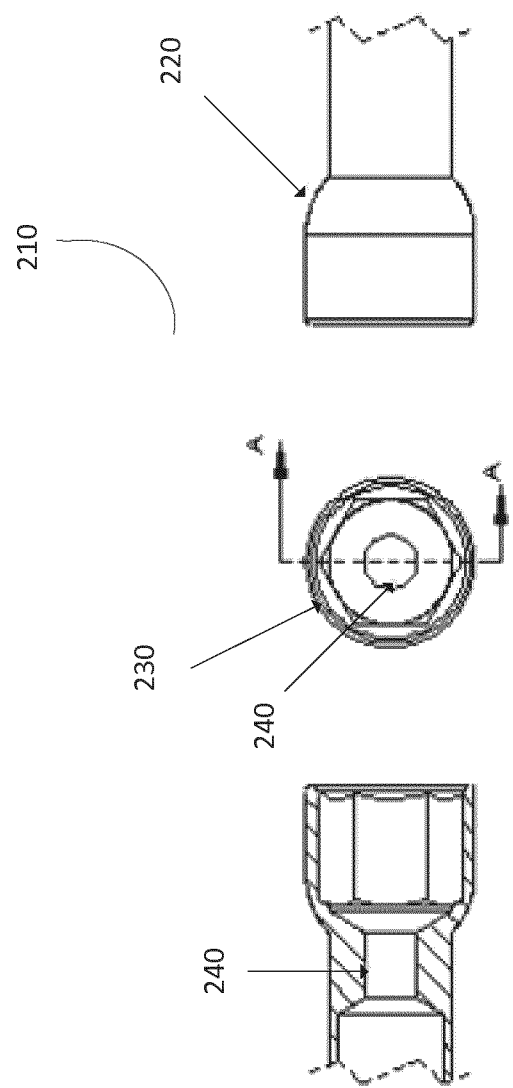

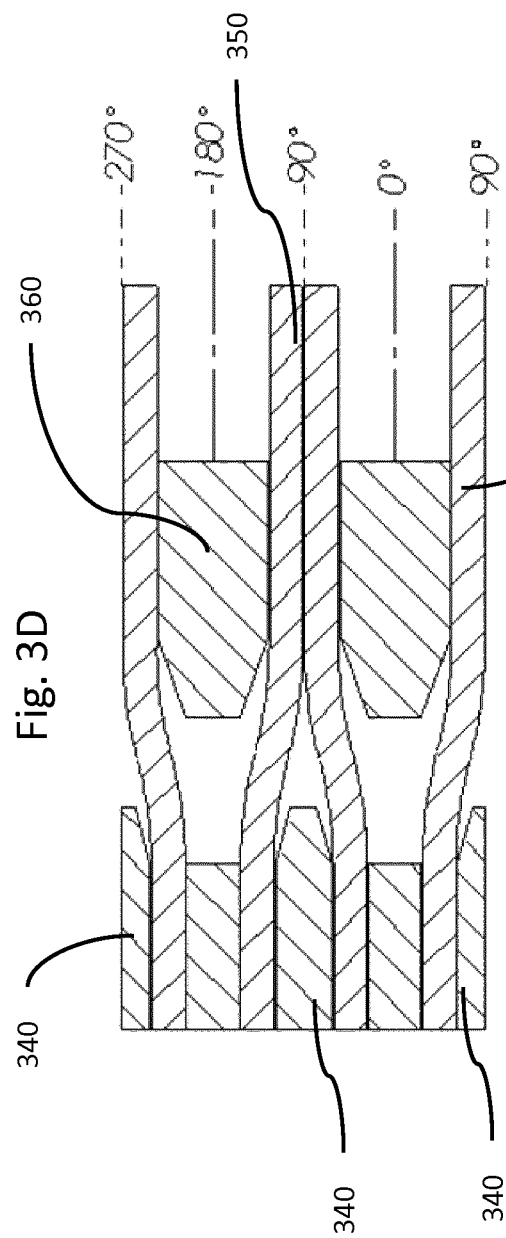
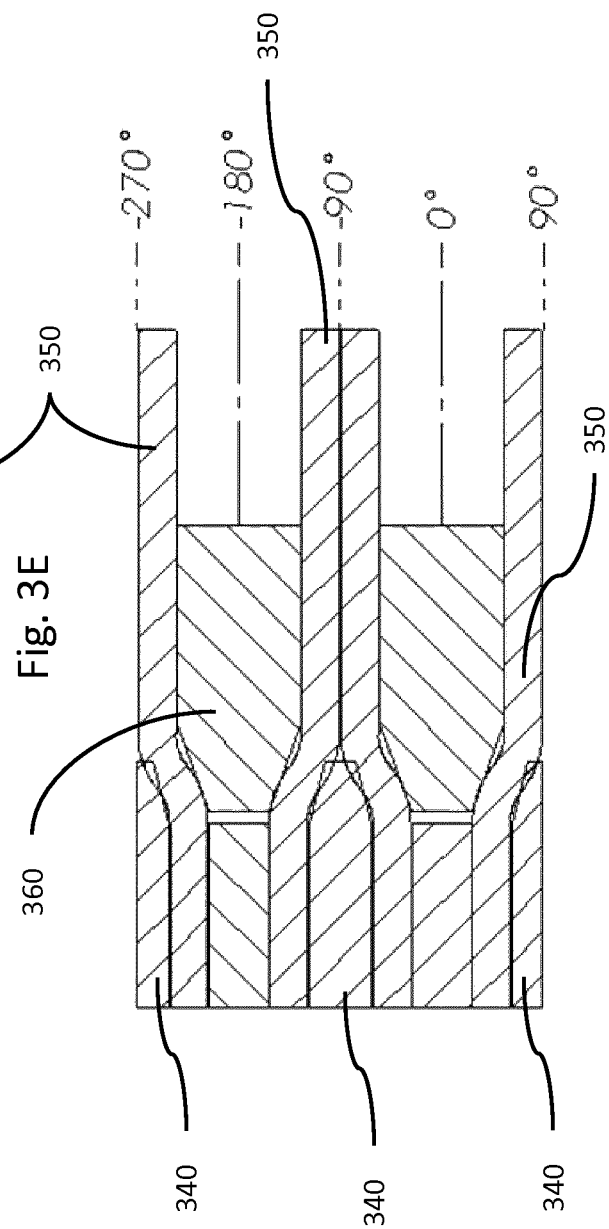

SYSTEMS AND METHODS FOR INTERMEDULLARY BONE FIXATION

CROSS-REFERENCES TO RELATED PATENT APPLICATIONS

This application is a continuation of U.S. patent application Ser. No. 15/519,148, filed on Apr. 13, 2017 and entitled "SYSTEMS AND METHODS FOR INTERMEDULLARY BONE FIXATION" which is a U.S. national stage filing under 35 U.S.C § 371 of International Application No. PCT/US2015/055441, filed Oct. 14, 2015 and entitled "SYSTEMS AND METHODS FOR INTERMEDULLARY BONE FIXATION", which claims priority under 35 U.S.C. § 119(e) to U.S. Provisional Patent Application No. 62/063,526, filed Oct. 14, 2014, the entire contents of all of which are herein incorporated by reference in their entirety.

International Application No. PCT/US2015/055441 relates to U.S. Provisional Application No. 61/949,177, titled "Shape Adaptable Intramedullary Fixation Device," filed on Mar. 6, 2014. International Application No. PCT/US2015/055441 further relates to U.S. patent application Ser. No. 14/300,752, titled "Intramedullary Fixation System for Management of Pelvic and Acetabular Fractures," filed on Jun. 10, 2014, which is a continuation of U.S. patent application Ser. No. 14/357,917, which is the U.S. National Stage Entry of International Application No. PCT/CA2012/050808, filed Nov. 14, 2012, which in turn claims the benefit of and priority to U.S. Provisional Patent Application 61/559,609, filed Nov. 14, 2011. The entire contents of the foregoing applications are herein incorporated by reference.

BACKGROUND

The following description is provided to assist the understanding of the reader. None of the information provided or references cited is admitted to be prior art.

The human skeleton has more than two hundred bones that have a range of shapes and dimensions. When a bone is fractured it may be completely fractured or partially fractured in any number of ways (crosswise, lengthwise, in multiple pieces). The unique geometry of each bone can make it difficult to properly fix the bone while it heals.

SUMMARY

The foregoing summary is illustrative only and is not intended to be in any way limiting. In addition to the illustrative aspects, embodiments, and features described above, further aspects, embodiments, and features will become apparent by reference to the following drawings and the detailed description.

Systems and methods for intermedullary bone fixation are described herein such as shape conforming implantable bone fixation device. In one aspect, an apparatus for intermedullary bone fixation is provided. The apparatus includes a main body having a flexible state and a rigid state. The apparatus further includes a proximal interface coupled to a proximal end of the main body to anchor the fixation device to an exterior surface of the bone and a distal interface coupled to a distal end of the main body to anchor the fixation device to an interior cavity of the bone. The apparatus further includes a locking interface configured to convert the main body from the flexible state to the rigid state, wherein the locking interface is coupled to the proximal interface.

In an embodiment, the main body includes a series of beads, and each bead in the series of beads includes a central bore and three or more fiber bores positioned around the central bore. The three or more fiber bores may house a three or more fibers that run a length of the main body. In an embodiment, the three or more fibers are axially fixed to the distal interface in the rigid state and the flexible state. The three or more fibers are in a fixed position at the proximal interface during the rigid state. In an embodiment, the series of beads of the main body can flex in one or more axis of motion during the flexible state.

In some embodiments, each bead includes a pair of lobes positioned at opposing ends of the respective bead and extending perpendicular from a first surface of the respective bead. Each bead may further include a pair of sockets formed into a second surface of the respective bead and positioned at opposing ends of the respective bead. The pair of sockets is configured to receive the pair of lobes of a preceding bead in the series of beads to form the series of beads. In an embodiment, each bead includes a central pivot point on the first surface of the respective bead that contacts a subsequent bead in the series of beads. The first surface of each bead can be configured to limit a bead to bead angulation in the series of beads to a pre-determined angle. The pre-determined angle may correspond to a minimum bend radius of the fixation device.

In an embodiment, the proximal interface includes an exterior surface that connects to the exterior bone surface and an interior surface configured to receive a driving tool. The proximal interface may include at least one of a hex, hexalobe, or a star pattern. In some embodiments, the internal surface of the proximal interface includes an access point to connect the locking interface to a driving tool when the driving tool is inserted into the proximal interface. The proximal interface may include a threaded internal surface to connect with the locking interface and a threaded exterior surface to connect with a bone surface. The threaded exterior surface may have a lower or higher pitch than the threaded internal surface.

In an embodiment, the locking interface includes a locking screw, a threaded portion, an outer shell housing a pair of fibers, a locking ram, and a locking face. The locking screw can be configured to receive a driving tool via an access point in the proximal interface. In an embodiment, the locking screw is configured to advance the locking ram and the locking ram is configured to rotate each fiber of the pair of fibers housed in the outer shell in opposing directions. A distal end of the locking ram may include a pair of faces configured to rotate the pair of fibers. The contour of the locking face can be the same as a contour of the pair of faces of the distal end of the locking ram. In an embodiment, the pair of faces of the distal end of the locking ram clamp the pair of fibers to the locking face in the rigid state.

In some embodiments, the locking interface includes a series of plates. Each plate in the series of plates includes a central bore and a pair of fiber bores to house a pair of fibers. When the central bore of each plate is offset relative to the central bore of a subsequent plate in the series of plates, the fixation device is in the flexible state. In the flexible state, the pair of fiber bores of each plate is inline relative to the pair of fiber bores of a subsequent plate. In an embodiment, a locking pin inserted through the central bore of each plate when the fixation device is in the rigid state. In the rigid state, the central bore of each plate is inline relative to the central bore of a subsequent plate in the series of plates and the pair of fiber bores of each plate is offset relative to the pair of fiber bores of a subsequent plate.

In an embodiment, the locking interface includes a locking screw, an interior body comprising an externally tapered shape, and an outer body includes an internally tapered shape. The interior body may include a central bore to receive a guide wire and a plurality of fiber bores to house a plurality of fibers. A distal end of the locking screw may include a cap configured to contact the interior body to advance the interior body to a tapered portion of the outer body when the locking screw is rotated clockwise. In some embodiments, the locking screw is configured to retract the interior body when the locking screw is rotated counter clockwise.

In an embodiment, the distal interface includes a threaded outer surface to anchor the fixation device to the interior cavity of the bone when the fixation device is installed in the interior cavity of the bone and a central bore.

In another aspect, a method for delivering a fixation device to a bone of a patient is provided. The method includes a delivering the fixation device in a flexible state into an interior cavity of the bone via an access point in the bone. The bone includes a fracture. The method further includes rotating a proximal end of the fixation device using a driving tool to secure a distal end of the fixation device into the interior cavity of the bone. The proximal end may be rotated until the proximal end is flush with the access point of the bone. The method further includes actuating a locking interface of the fixation device via the proximal interface to convert the fixation device from a flexible state to a rigid state.

The method further includes accessing a surface of the bone via a cannula inserted into a soft tissue region of the patient and establishing the access point in a surface of the bone to insert the fixation device into the interior cavity of the bone. A guide can be delivered to the interior cavity of the bone via the access point and is inserted to a pre-determined point past the fracture in the bone. A diameter of the interior cavity of the bone can be increased using a reamer installed over the guide.

In an embodiment, the fixation device includes a main body including a series or beads, a proximal interface coupled to a proximal end of the main body; a distal interface coupled to a distal end of the main body; and a locking interface configured to convert the fixation device from a flexible state to a rigid state. Each bead in the series of beads can include a central bore and three or more fiber bores positioned around the central bore. Three or more fibers run a length of the main body and each of the three or more fiber bores houses one of the three or more fibers. In an embodiment, the three or more fibers are axially fixed to the distal interface in the rigid state and the flexible state.

The method further includes converting the three or more fibers to a fixed position at the proximal interface in the rigid state. In some embodiments, each bead includes a pair of lobes positioned at opposing ends of the respective bead and extending perpendicular from a first surface of the respective bead. Each bead may further include a pair of sockets formed into a second surface of the respective bead and positioned at opposing ends of the respective bead. The pair of sockets are configured to receive the pair of lobes of a preceding bead in the series of beads to form the series of beads. Each bead may include a central pivot point on the first surface of the respective bead that contacts to a subsequent bead in the series of beads.

In an embodiment, the first surface of each bead is configured to limit a bead to bead angulation in the series of beads to a pre-determined angle, the pre-determined angle corresponding to a minimum bend radius of the fixation device. The method further includes securing the proximal interface to an exterior surface of the bone such that the proximal interface is flush with the access point of the bone. The method further includes rotating the proximal interface to engage a threaded exterior surface of the proximal interface with the exterior surface of the bone. In some embodiments, the proximal interface includes at least one of a hex, hexalobe, or a star pattern to receive a driving tool. An internal surface of the proximal interface may include an access point to connect the locking interface to the driving tool when the driving tool is inserted into the proximal interface. The method further includes actuating the locking interface via the interior surface of the proximal interface to convert the fixation device from a flexible state to a rigid state. The locking interface can move independent of the proximal interface.

In an embodiment, the proximal interface includes a threaded internal surface and the threaded exterior surface has a higher pitch than the threaded internal surface. The method further includes receiving, by a locking screw of the locking interface, a driving tool via an access point in the proximal interface and rotating the locking screw to actuate a locking ram of the locking interface. The method further includes advancing the locking ram to rotate each fiber of a pair of fibers housed in the locking interface. The pair of fibers may be rotated from the flexible state to the rigid state and vice-versa. A distal end of the locking ram may include pairs of faces configured to rotate pairs of fibers. The method further includes clamping of fibers, between the face of the locking interface, and the ram of the locking interface in the rigid state.

In an embodiment, the locking interface includes a series of plates and each plate in the series of plates includes a central bore and a pair of fiber bores to house a pair of fibers. In some embodiments, the central bore of each plate is offset relative to the central bore of a subsequent plate in the series of plates when the fixation device is in the flexible state and the pair of fiber bores of each plate is inline relative to the pair of fiber bores of a subsequent plate when the fixation device is in the flexible state. In some embodiments, the series of stacked plates includes a locking pin inserted through the central bore of each plate when the fixation device is in the rigid state. The central bore of each plate can be inline relative to the central bore of a subsequent plate in the series of plates when the fixation device is in the rigid state and the pair of fiber bores of each plate can be offset relative to the pair of fiber bores of a subsequent plate when the fixation device is in the rigid state.

The method further includes actuating an interior body of the locking interface with a distal end of a locking screw of the locking interface and advancing, by the locking screw, the interior body to a tapered portion of an outer body of the locking interface when the locking screw is rotated clockwise. The method may include retracting, by the locking screw, the interior body when the locking screw is rotated counter clockwise. The method further includes anchoring a threaded outer surface of the distal interface to the interior cavity of the bone.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are; therefore, not to be considered limiting of its scope, the disclosure will be described with additional specificity and detail through use of the accompanying drawings.

FIGS. 2a-2c depict various views of a proximal interface of a fixation device in accordance with an illustrative embodiment.

FIGS. 3d and 3e depict a cross sectional locking interface in unlocked and locked states, respectively, in accordance with an illustrative embodiment.

DETAILED DESCRIPTION

Figure 1:
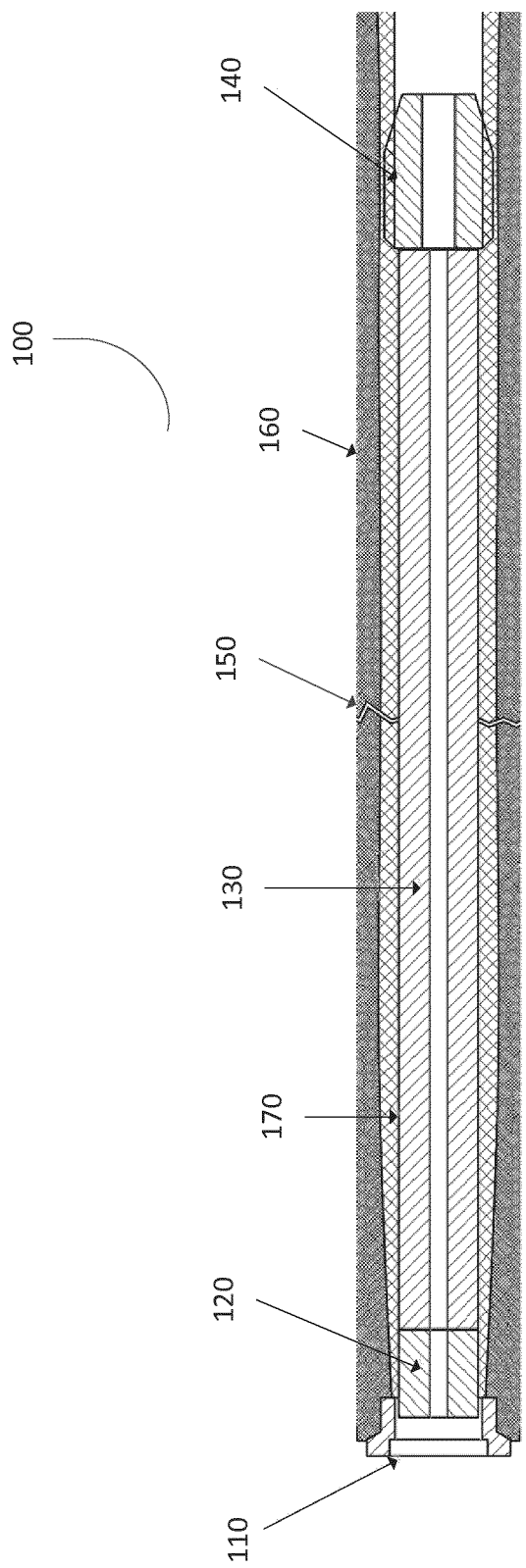
FIG. 1 depicts a fixation device for fixing a bone fracture in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

The unique geometry and/or curvature of a bone can make it difficult to properly fix a bone while it is healing. For example, stable pelvic ring injuries rarely result in major long-term problems because their initial treatment is straightforward and their recovery uneventful and complete. However, patients with unstable pelvic ring injuries are more challenging to treat and may suffer from complications. For example, 25% to 75% of patients with an unstable pelvic fracture will suffer some form of incomplete recovery, according to a number of studies. For cases that are treated surgically, mal- and non-unions can still occur. Inadequate reduction and fixation can lead to a number of problems, including pain, pelvic tilt, impaired gait, leg-length discrepancy, scoliosis, difficulties in sitting, and restrictions in activities of daily life, sexual dysfunction, urinary system complaints, and non-unions with implant breakage.

Bone fractures in general may occur in both long bones, where internal fixation may be performed using long straight internal fixation mechanisms, or in bones with some complex curvature, where use of a straight internal fixation device becomes limited based on the bone radius of curvature. The minimally invasive internal fixation of arched bone structures, specifically where straight screws cannot provide proper fixation, or access limits the installation of straight screws, or necessitates invasive procedures to apply plates or external fixation devices.

The present disclosure is directed to an apparatus such as a fixation device for a bone fracture in a patient. The fixation device includes an elongated structure with a proximal bone interface, a shape-locking interface, a main body, and a distal bone interface. The main body is capable of converting from a flexible state, via the shape locking interface, in which the main body of the device can flex in one or more axis, to a rigid state. In the rigid state, the fixation device can support the loads required in the healing phase of patient treatment. The fixation device may also revert into the flexible state for the purpose of device removal. The conversion from one state to another provides the compliance needed to attain access into and thru arched internal bone passages from a single point, and after conversion maintains the final arched geometry necessary to maintain the relative position of the fractured bone segments. The position of bone fragments along the axis of the fixation device is maintained by the proximal and distal bone interfaces.

FIG. 1 depicts a fixation device 100 for fixing a bone fracture in accordance with an illustrative embodiment. The fixation device 100 includes a proximal interface 110, a locking interface 120, a main body 130, and a distal interface 140. A bone fracture 150 may be present type in the hard exterior surface of a bone 160, such as the cortical bone. In other embodiments, the bone fracture may be present in a cancellous bone region of the bone 160. In some embodiments, the bone fracture 150 is present through both the cortical bone and the cancellous bone.

In an embodiment, the term "fix" or "fixing" as used herein may refer to providing support to a bone and/or making a bone firm, stable, or stationary using a fixation device such as the fixation device 100 illustrated in FIG. 1. For example, the term fix or fixing can be the act of holding two or more pieces or fragments of bone in place relative to each other. In an embodiment, the fixation device 100 can be used in an internal fixation procedure which is an operation in orthopedics that involves the surgical implementation of implants for the purpose of repairing a bone 160. During internal fixation, a fixation device, such as the fixation device 100 illustrated in FIG. 1, is provided to a fractured bone to fix the bone 160 and aid in supporting load during the healing phase. In some embodiments, internal fixation devices may also include plates, screws, intermedullary (IM) nails or rods, cannulated screws, conventional hip screws, and ancillary trauma devices, such as pins, wires, cables, general screws, and staples.

In an embodiment, the fixation device 100 is inserted into an interior cavity 170 of the bone 160 to fix the bone fracture 150. The interior cavity 170 may refer to a medullary cavity of a bone or a cancellous bone region of a bone. In some embodiments, the fixation device 100 is an intermedullary (IM) device used to treat bone fractures. The fixation device 100 is delivered so that it is contact with the interior surface of the bone 160. In some embodiments, the fixation device 100 is even with, or flush with, the interior surface of the bone 160. In other embodiments, the fixation device 100 is delivered adjacent to an exterior surface of the bone 160.

The fixation device 100 may be inserted up to a predetermined depth in the interior cavity 170 that is past the bone fracture 150. In some embodiments, the fixation device 100 is inserted into the interior cavity 170 of the bone 160 such that the distal interface 140 is beyond the bone fracture 150. In one embodiment, the fixation device 100 is inserted into the interior cavity 170 of the bone 160 and aligned with the bone 160 so that the bone fracture 150 is positioned at a half-way point (i.e., equidistant) between the proximal interface 110 and the distal interface 140. The position of bone fragments along the axis of the fixation device 100 is maintained by the proximal interface 110 and the distal bone interface 140.

In an embodiment, the proximal interface 110 is a proximal end of the fixation device 100 and may refer to the end of the fixation device that is closest to the person implanting the fixation device 100. The proximal interface 110 provides an interface for various tools used to install, advance, and retract the fixation device 100 from the interior cavity 170. The proximal interface 110 can be coupled to a proximal end of the fixation device 100 and coupled to the locking interface 120. The proximal interface 110 will be described in greater detail below with respect to FIGS. 2a-2d.

In an embodiment, the locking interface 120 is configured to convert the main body 130 of the fixation device 100 from a flexible state to a rigid state. A flexible state refers to a state in which the fixation device 100 is more flexible than in the rigid state. A rigid state refers to a state in which the fixation device 100 is less flexible than in the flexible state. The rigid state may refer to a state in which the fixation device 100 has a lower degree of flexion as compared to the flexible state. The degree of flexion for the fixation device in the rigid state may vary depending on the architecture and/or geometry of the bone 160 the fixation device 100 is fixing. In one embodiment, converting from the flexible state to the rigid state may refer to changing a flexion degree of the fixation device 100. In the rigid state, the fixation device 100 may still have some degree of flexion; however the fixation device 100 can support the loads as required in the healing phase of patient treatment.

In an embodiment, the locking interface 120 is positioned between the proximal interface 110 and the main body 130. When the locking interface 120 is actuated by a tool via the proximal interface 110, the locking interface 120 causes the main body 130 to convert from the flexible state to the rigid state. In some embodiments, the locking interface 120 is a component of the proximal interface 110. The locking interface 120 will be described in greater detail below with respect to FIGS. 3a-3f.

In an embodiment, the main body 130 is positioned between the locking interface 120 and the distal interface 140. The main body 130 has a flexible state and a rigid state. In a flexible state, the components of the main body 130 can flex in one or more axes of motion to allow the fixation device to be installed thru arched internal bone passages from a single point. In the rigid state, the components of the main body 130 support the loads required by the bone 160 to which the fixation device 100 is coupled. After conversion from the flexible state to the rigid state, the main body 130 maintains the final arched geometry necessary to maintain the relative position of the fractured bone segments. The main body 130 will be described in greater detail below with respect to FIGS. 4a-4d.

In an embodiment, the distal interface 140 is a distal end of the fixation device 100 and may refer to the end of the fixation device 100 that is farthest away from the person implanting the fixation device 100. The distal interface 140 anchors the fixation device 100 to the interior cavity 170. The distal interface 140 will be described in greater detail below with respect to FIGS. 5a-5b.

Various embodiments of the proximal interface 210 are now shown (FIGS. 2a-2c). For example, FIG. 2a depicts a cut-away view of the proximal interface 210. In an embodiment, the proximal interface 210 anchors the proximal end of the fixation device to an outer (i.e., exterior) surface of the bone. The proximal interface 210 may be an individual component or a set of components that together form the proximal interface 210. In some embodiments, the proximal interface 210 includes a set of components that form an exterior surface 220 that contacts the outer surface of the bone. The exterior surface 220 may include a step configuration to mate to the outer surface of the bone and form a seal around an access point drilled into the outer surface of the bone. In some embodiments, the proximal interface 210 may be connected to the outer surface of the bone using a set of pins and bores drilled through the bone in the proximal interface 210. In other embodiments, the exterior surface 220 is threaded and engages the outer surface of the bone or an interior surface of the access point.

To engage the outer surface, the proximal interface 210 is rotated using a driving tool. In an embodiment, the proximal interface 210 includes an interior surface 230 that includes various configurations to receive and engage a driving tool. For example, FIG. 2b depicts a top view of the proximal interface 210 with a hex pattern to receive the driving tool. In other embodiments, the interior surface 230 of the proximal interface 210 may include a star pattern or a threaded pattern or a hexalobe pattern to receive the driving tool. The driving tool is inserted into the proximal interface 210 and rotated until the proximal interface 210 is even with or flush with the access point drilled into the outer surface of the bone.

The proximal interface 210 can transfer energy (i.e., torque, compression, tension) from the driving tool to the other components of the fixation device (e.g., the locking interface, the main body, the distal interface). In an embodiment, the proximal interface 210 and the distal interface transfer load from the bone to the fixation device and vice versa.

In an embodiment, the interior surface 230 of the proximal interface 210 includes two portions, a first portion (proximal end) to actuate the proximal interface 210 and a second portion (distal end) to allow access to the locking interface thru the proximal interface 210. For example, the proximal interface 210 can rotate independent of the locking interface, the main body, the distal interface, or the device in the bone in general. In one example, the engagement with and/or movement of the locking mechanism/interface does not change the shape, position, or length of the fixation device. The proximal interface 210 can have a driving torque feature in the first portion to allow the proximal interface 210 to be advanced into position and engage with the surface of the bone without actuating the locking interface. The interior surface 230 can be rotated over the fixation device and up and into the bone.

The second portion of the interior surface 230 can include inner threads to engage with the locking interface or the main body. In an embodiment, the proximal interface 210 allows passage of some portion of the locking mechanism through its center, such that the locking mechanism, distal to the proximal interface 210, may be actuated while holding the proximal interface 210 steady relative to the bone surface. The proximal interface 210 may include a central bore or access point 240 to provide a pathway for a driving tool to engage the locking interface thru the proximal interface 210. FIG. 2c depicts a side view of the proximal interface 210.

Figure 2D:
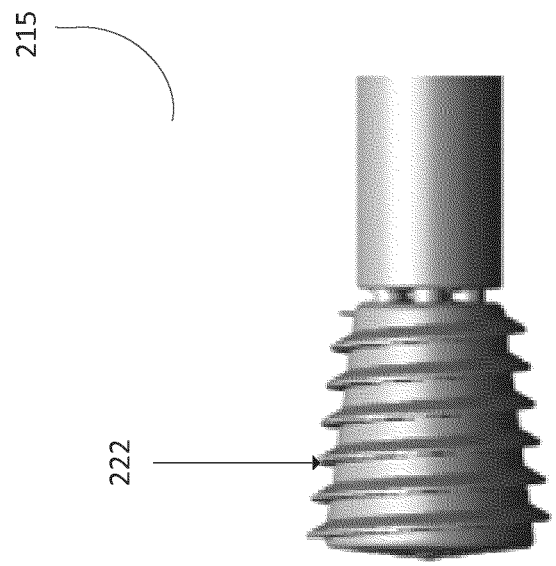
FIG. 2d depicts an alternative embodiment of a proximal interface in accordance with an illustrative embodiment.

Now referring to FIG. 2d; FIG. 2d depicts an alternative embodiment to the proximal interface 210. Proximal interface 215 of FIG. 2d includes a proximal assembly having a proximal threaded exterior surface 222. The proximal threaded exterior surface 222 can engage with the surface of the bone, including the interior surface or the outer surface of the bone to secure the fixation device on one end to the bone. The proximal threaded exterior surface 222 may include cutting threads. The proximal interface 215 may include internal threads that engage with a locking interface or a main body of a fixation device. The threads on the proximal threaded exterior surface 222 may be of a higher pitch than the threads on the distal surface, such that rotation of the proximal interface 215 when engaged with the bone causes compression of the material engaged between the threaded proximal exterior surface 222 of the proximal interface 215 and threads of the distal interface. In other embodiments, the threads on the proximal threaded exterior surface 222 may be of a lower pitch than threads on a surface of the distal interface, such that the bone fragments would be forced together as both threads interact with the bone. In an alternative embodiment, embodiment, the pitches of the threads may not be different.

Figure 3A:
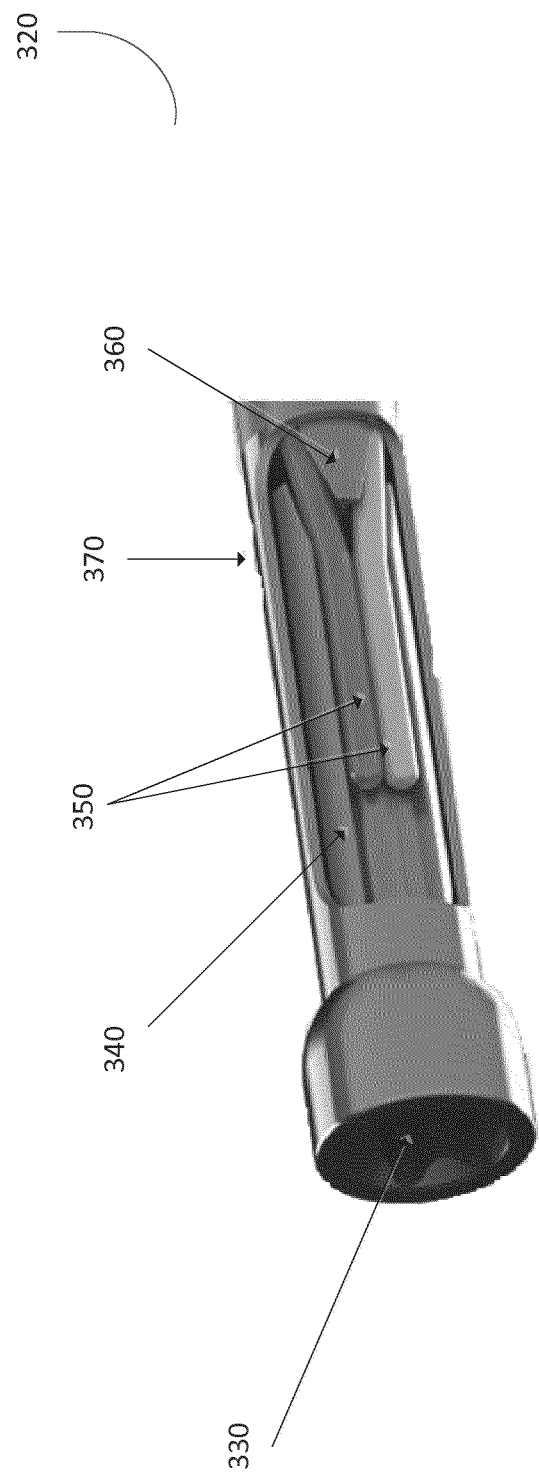
FIG. 3a depicts a locking interface of the fixation device in accordance with an illustrative embodiment.

FIG. 3a depicts a locking interface 320 in accordance with an illustrative embodiment. The locking interface 320 includes a locking screw 330, a ram 340, a plurality of fibers 350, and a locking face 360. In an embodiment, the locking screw 330 can move through the locking interface 320 to actuate the ram 340. For example, the locking screw 330 can be advanced against the ram 340 by a driving tool inserted into the proximal interface. The ram 340 can move each pair of fibers 350 radially inside an outer shell 370 in opposing directions. For example, for each fiber pair 350, the ram 340 moves one fiber 350 clockwise and the other fiber 350 counter-clockwise. The distal end of the ram 340 has pair of faces that can be defined by the position of the fibers 350 in the unlocked position plus some radial offset, a transition length, and position of the fibers 350 in the locked position. In an embodiment, the ram 340 is advanced until the fibers 350 are in contact with the locking face 360.

The locking face 360 can have a similar or same contour as the contour of the distal end face of the ram 340, plus some offset equal to a percentage of the fiber diameter. The net space remaining between the ram 340 and the locking face 360 is a percentage of the fiber diameter, so that a controlled amount of fiber pinch can be produced in the actuated state. The faces of both the ram 340 and the locking face 360 may be of a smooth profile, or stepped profile, as illustrated in FIGS. 3b-3c.

Figure 3B:
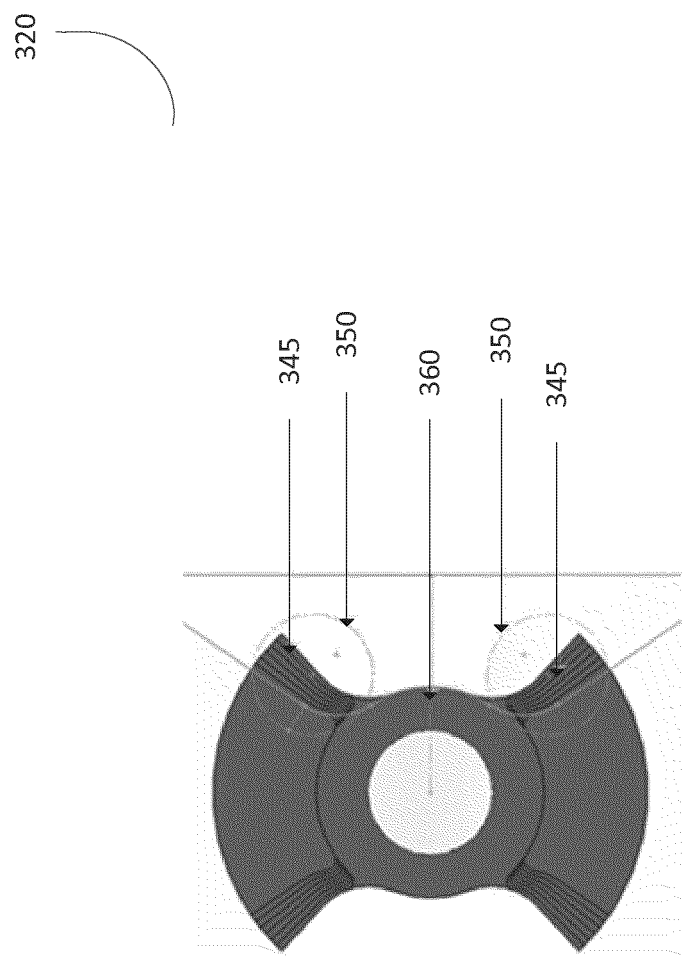
FIG. 3b depicts a locking interface in an unlocked state in accordance with an illustrative embodiment.
Figure 3C:
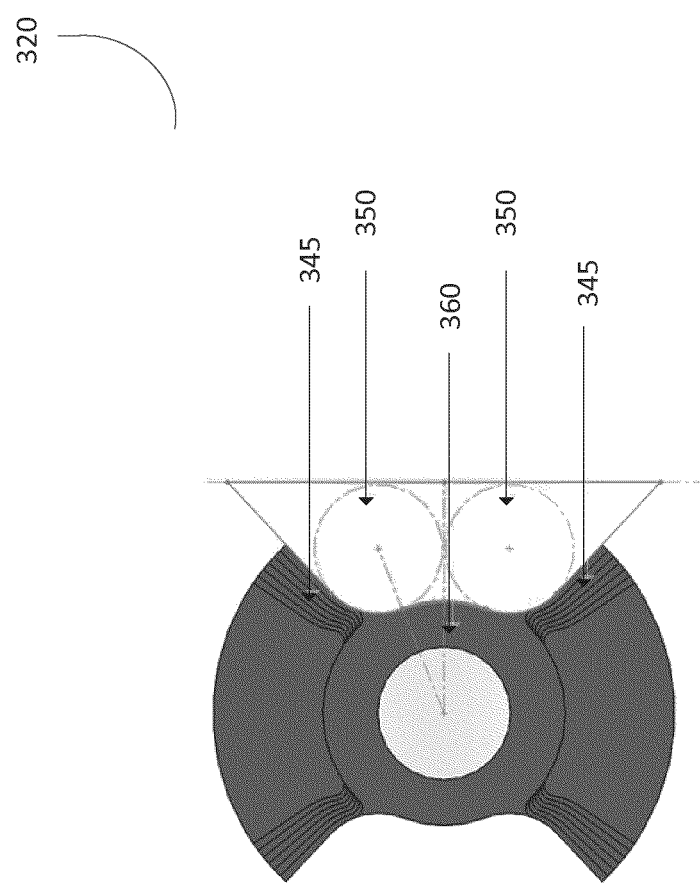
FIG. 3c depicts a locking interface in a locked state in accordance with an illustrative embodiment.

In more detail, FIGS. 3b and 3c depict a step configuration for both the pair of faces 345 of the ram 340 and the locking face 360. FIG. 3b shows the locking face 360 in a flexible state (unlocked state), where the fibers 350 are spaced a certain distance from each other to allow movement in one or more axes of motion relative to the other fibers 350. The spacing of the fibers 350 in the flexible state can correspond to the flexibility or bend radius of the fixation device when it is in the flexible state. FIG. 3c shows the locking face 360 in the rigid state (locked state), where the fibers 350 are clamped together using the faces 345 of the ram 340 and the locking face 360 to limit or restrict the motion of the fibers relative to each other. The step configuration adds additional fiber grip in the locked state. The resulting interference between the components when the locking screw 330 is driven fully into place creates a clamping force that holds each fiber 350 in its position, without any change in its position relative to the other fibers 350 in the assembly.

In other embodiments, the locking interface 320 includes a series of stacked plates. Each plate can have fiber bores (holes) for fibers 350 offset in an alternating pattern from a free fiber position and a central bore (hole) to receive a guide wire or locking pin. In the unlocked position (i.e., flexible state), the center bores in the plates are offset relative to each other and the fiber holes are inline relative to each other, allowing the fibers 350 free movement. In the locked state (i.e., the rigid state), a locking pin can be inserted into the center bore of the plates extending through all of the plates in the series of plates and forcing the plates inline relative to the center-bore. The fiber bore holes and fibers are offset relative to each other in the locked state and this creates a gripping action on the fibers 350, holding each fiber 350 in its position, without any change in its position relative to the other fibers 350 in the assembly.

FIGS. 3d and 3e depict a cross sectional locking interface in unlocked and locked states, respectively, in accordance with an illustrative embodiment. For example, FIGS. 3d and 3e show the ram 340, the locking face 360, and the fibers 350. FIG. 3d shows the unlocked state, and FIG. 3e shows the locked state where the fibers 350 (or cables) are pinched in order to lock the fibers 350 into position.

Figure 3F:
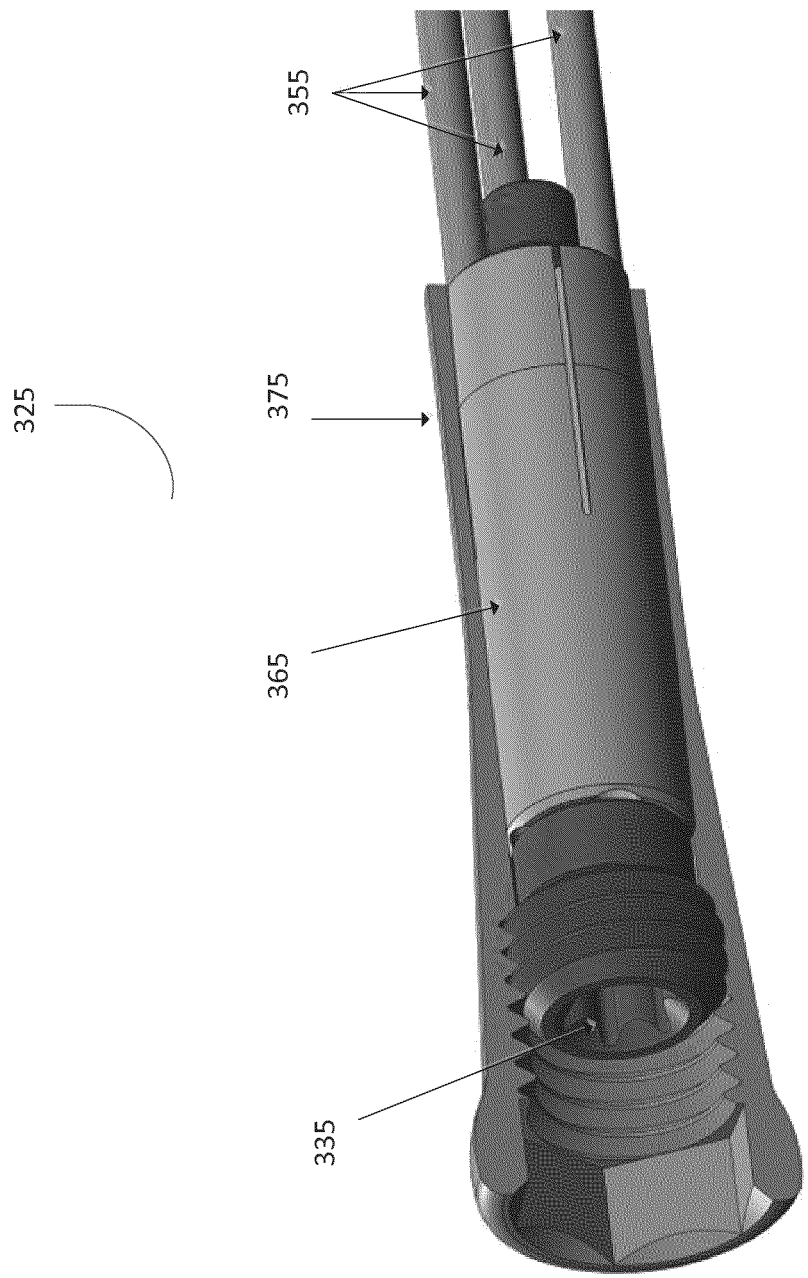
FIG. 3f depicts an alternative embodiment of a locking interface in accordance with an illustrative embodiment.

In FIG. 3f, an alternative embodiment of a locking interface 325 is shown. The locking interface 325 includes a driving screw (locking screw) 335, an interior body 365, an outer body 375, and a plurality of fibers 355. In an embodiment, the interior body 365 includes fiber bores to house the plurality of fibers 355 and is externally tapered. The outer body 375 may be internally tapered. The tapered section on the internal body 365 is wrapped around each fiber bore such that when advanced to a tapered section in the outer body 375, the internal body 365 flexes inward, pinching the fibers 355.

In an embodiment, the locking screw 335 has a central bore or is cannulated to allow passage of a guide wire in the locked or unlocked state. The locking screw 335 can pass fully through the interior body 365. The locking screw 335 can have a retention cap on the distal end of the locking screw 335 to contact and engage the interior body 365. For example, rotation of the locking screw 335 in the clockwise direction can advance the interior body 365 to a locked state. Rotation of the locking screw 335 in the counterclockwise direction can retract or relieve the pressure on the interior body 365 causing it to retract to the unlocked state.

Figure 4A:
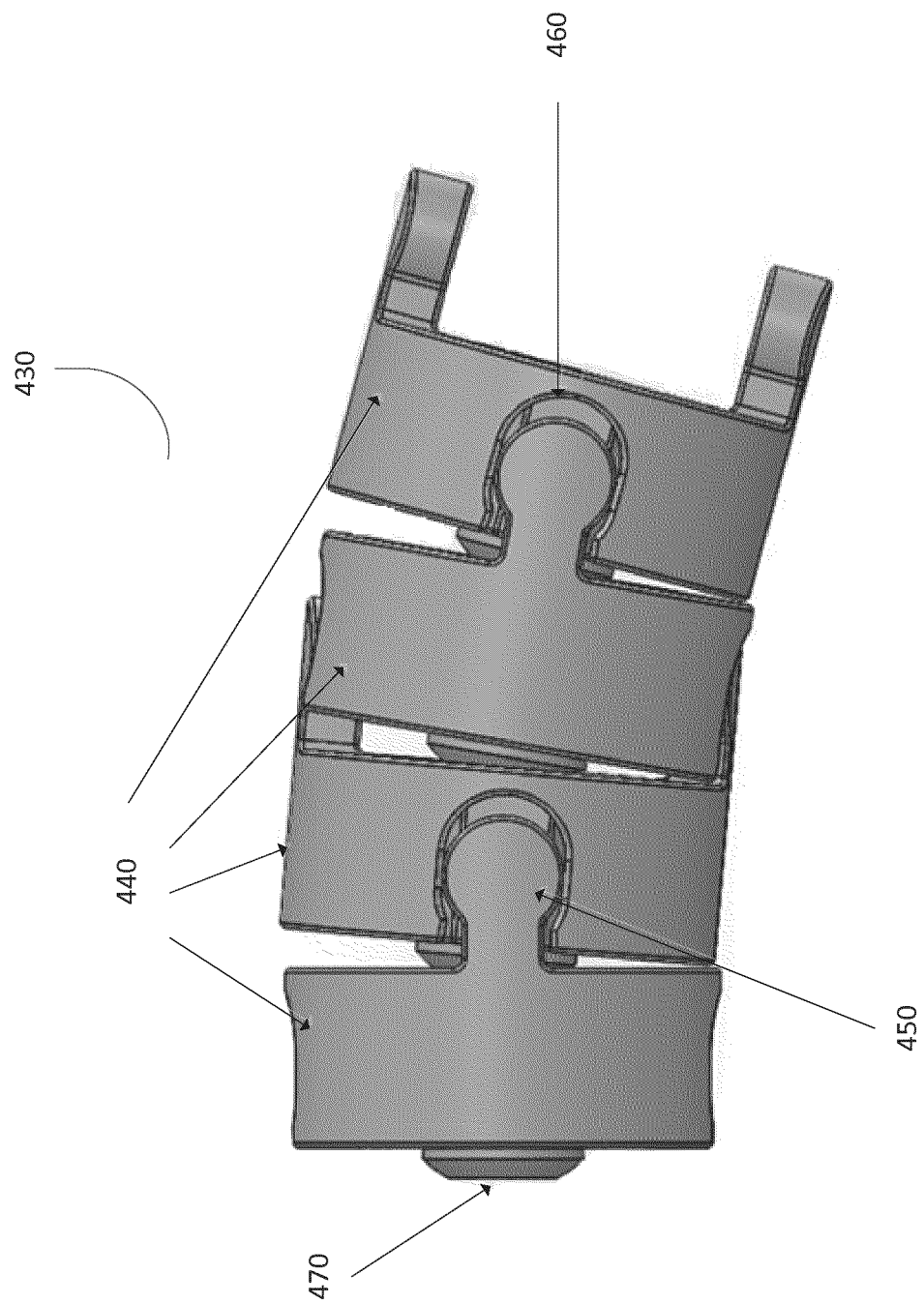
FIG. 4a depicts a main body of a fixation device in accordance with an illustrative embodiment.

FIG. 4a depicts a main body 430 in accordance with an illustrative embodiment. The main body 440 includes a series of beads 440 coupled together to form the main body 440. In an embodiment, the beads 440 include a pair of lobes 450, a pair of sockets 460, and a central pivot point 470. The body 430 may change shape from straight, where no relative angulation is present, to the approximation of a curvature as beads tilt upon the central pivot point 470. The main body 430 has a flexible state and a rigid state, independent of main body shape, controlled by the state of the locking mechanism in the proximal end 210.

To connect each bead 440 to a subsequent or preceding bead 440 in the series of beads, the pair of lobes 450 connects into a pair of sockets of a next bead 440. The beads 440 can be limited in axial movement by the configuration and dimensions of the lobes 450 and the sockets 460. Each lobe 450 in the pair of lobes can be located at opposing ends of bead 440. For example, the lobes 450 in a pair of lobes 450 may be equidistant from each other. In other embodiments, the lobes 450 may be offset a pre-determined degree relative to one another. The lobes 450 may extend perpendicular from a first surface of the bead to connect to the sockets 460.

In an embodiment, the sockets 460 are formed into a second surface of a bead 440. The second surface may be the opposite surface from the first surface of the bead 440. Each socket 460 in the pair of sockets can be located at opposing ends of the bead. For example, the sockets 460 in a pair of sockets 460 may be equidistant from each other. In other embodiments, the sockets 460 may be offset a pre-determined degree relative to one another.

In an embodiment, the central pivot point 470 is located at a central point on a second surface of the bead, for example the same surface as the sockets 460. The central pivot point 470 adjoins or contacts a next sequential bead 440 in the series of beads. The central pivot point 470 may include a central bore 480 formed through it.

Figures 4B, 4C, 4D:
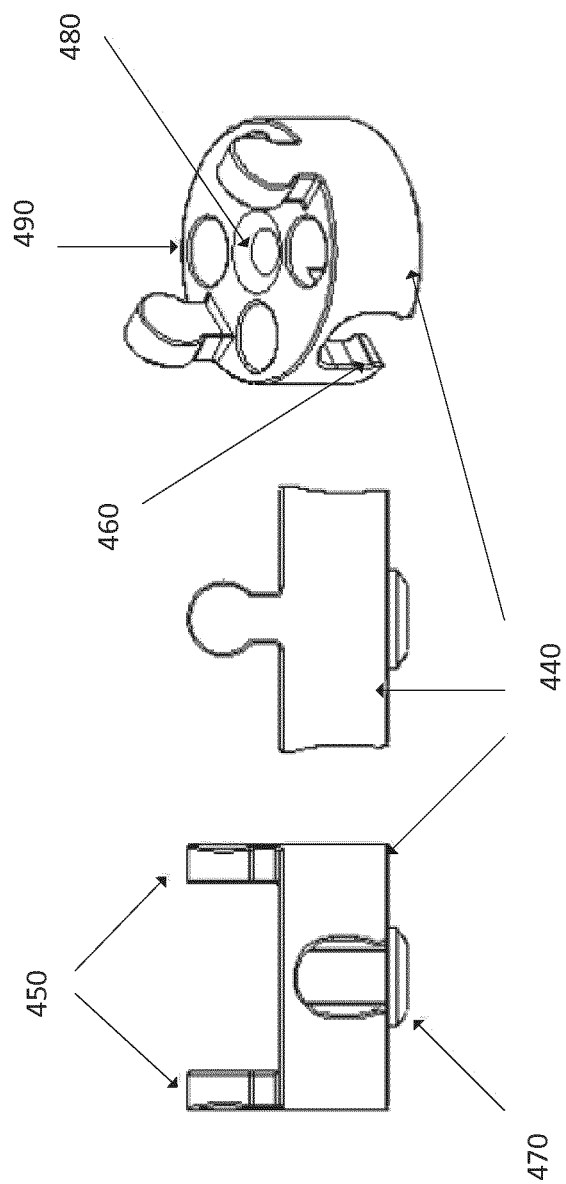
FIGS. 4b-4d depict various views of a bead of the main body of the fixation device in accordance with an illustrative embodiment.

FIGS. 4b-4d illustrate a bead 440 at different angles to show the configuration of the pair of lobes 450, the pair of sockets 460, and the central pivot point 470. FIG. 4b and FIG. 4c depict different side views of the bead 440. The pair of lobes 450 extends perpendicular from a plane of the first surface of the bead 440. The sockets 460 are formed into an opposite side, the second side of the bead. The pair of lobes 450 and the pair of sockets may be positioned along an edge or outer circumference of the bead 440.

FIG. 4d depicts a top view of the bead 440. As illustrated in FIG. 4d, each bead 440 includes a central bore 480 or a hollow core and fiber bores 490. The central bore 480 can receive a guide wire which can be used to direct a fixation device through an interior cavity of a bone. In one embodiment, each bead 440 has three fiber bores 490 to house fibers. In other embodiments, the number of fibers bores 490 may range from at least one to a number corresponding to the number of fibers to be used in the fixation device.

The beads 440 separate and support a series of tensile fibers that are housed within the fiber bores 490 of the beads 440. The main body 440 has two states that it can convert between, a flexible state and a rigid state. In the flexible state, the fibers are axially fixed to the distal interface only, with the fibers free to translate through their respective bores in each bead 440.

The surfaces of the beads can limit the bead to bead angulation to a pre-determined maximum angle, resulting in a device minimum bend radius. For example, the face of a bead 440 that surrounds an edge of the central pivot point 470 can limit the bead to bead angulation to a pre-determined maximum angle, resulting in a device minimum bend radius. In an embodiment, the beads have a fiber bores 490 spaced around the central bore 480 that maintain tensile fibers at a distance from the center of the bead 440, as well as in a specific radial position (i.e. at 0°, 60°, 120°, 180°, 240°, 300°, 360°). The tensile fibers members may terminate within the main body 430, or in members attached to either end of the main body 430, such as a proximal interface, a locking interface, or a distal interface. When the bead to bead angulation is limited, an additional advantage for recovery of a fracture is that the beads can transfer tensile load in addition to and/or instead of the cables or tensile fibers in the main body.

For example, in a rigid state, the fibers are fixed in position at the proximal interface and the translation of the fibers becomes limited. In some embodiments, the three fibers must be in place in the main body 430 to provide bead fixation about all planes of movement. In other embodiments, additional fibers may be added to provide additional strength, as well as a more uniform flexural stiffness in any bending axis with respect to the fibers pattern orientation. The fiber bores 490 in each bead 440 can form a lateral support for each fiber, keeping the fibers away from the neutral bending axis, such that when the rigid assembly experiences a transverse load, the transverse load creates a purely tensile load in any fiber on the opposite side of the bending axis from the transverse load. In an embodiment, the assembly of the fibers inside the fiber bores 490 of each bead provides a torque transmission capability when beads 440 are in close proximity, equal to the shear strength of that of the sum of at least two fibers, and at most the total number of fibers in the assembly.

Figure 5A:
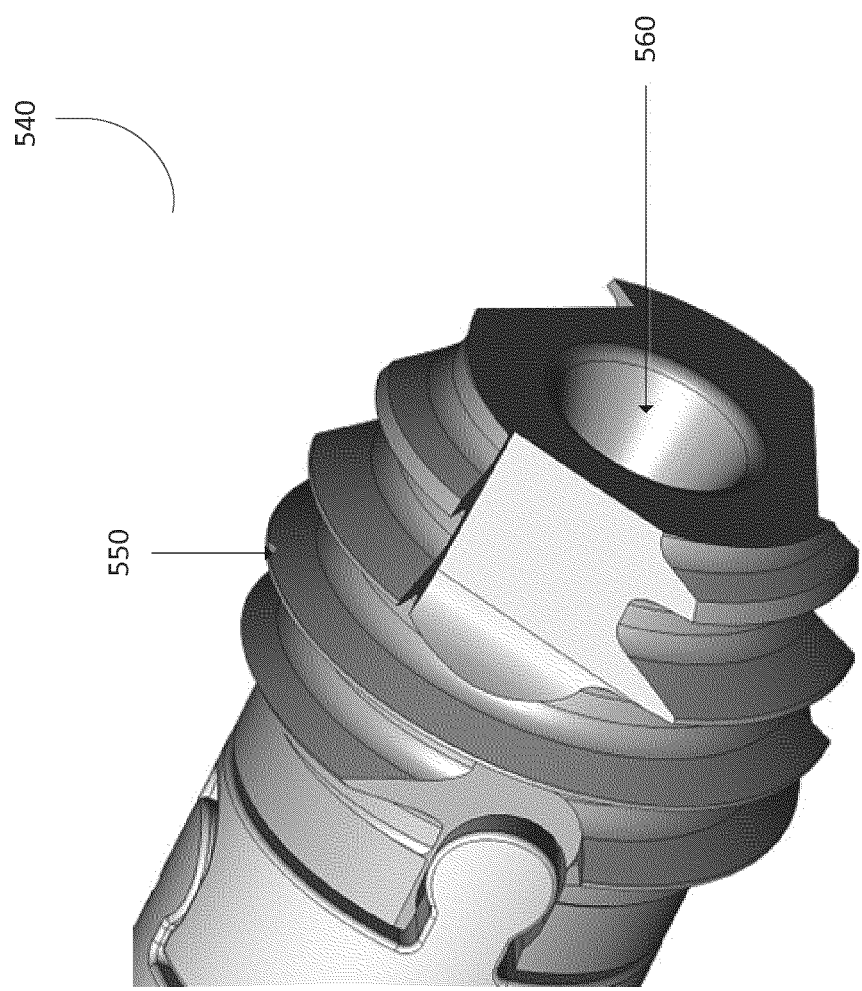
FIG. 5a depicts a distal interface of a fixation device in accordance with an illustrative embodiment.

Now referring to FIG. 5a, a distal interface 540 in accordance with an illustrative embodiment is shown. In an embodiment, the distal interface 540 anchors the distal end of a fixation device to an interior surface of a bone. For example, the distal interface 540 can be mated (engaged) into an interior cavity of the bone to secure the distal end of the fixation device to the bone. The distal interface 540 can transfer load from the bone to the fixation device and vice versa when attached to the bone.

The distal interface 540 may be an individual component or a set of components that together form an exterior surface that contacts the interior bone surface at the distal end of the fixation device. In an embodiment, the distal interface 540 includes a threaded exterior surface 550. The threaded surface 550 can engage and mate with the interior surface of the bone to connect the distal end of the fixation device top the bone. The threads of the threaded surface 550 can be configured in a geometry that allows retention of the distal interface 540 to the interior region of the bone. In an embodiment, the threaded exterior surface 550 includes different types of threads, including threads of different sizes. For example, in one embodiment, the threaded exterior surface 550 includes cutting threads that remove and direct tissues in front of threads at a major diameter of the body of the distal interface, reducing the torque required to drive the fixation device into the interior region of the bone.

Figure 5B:
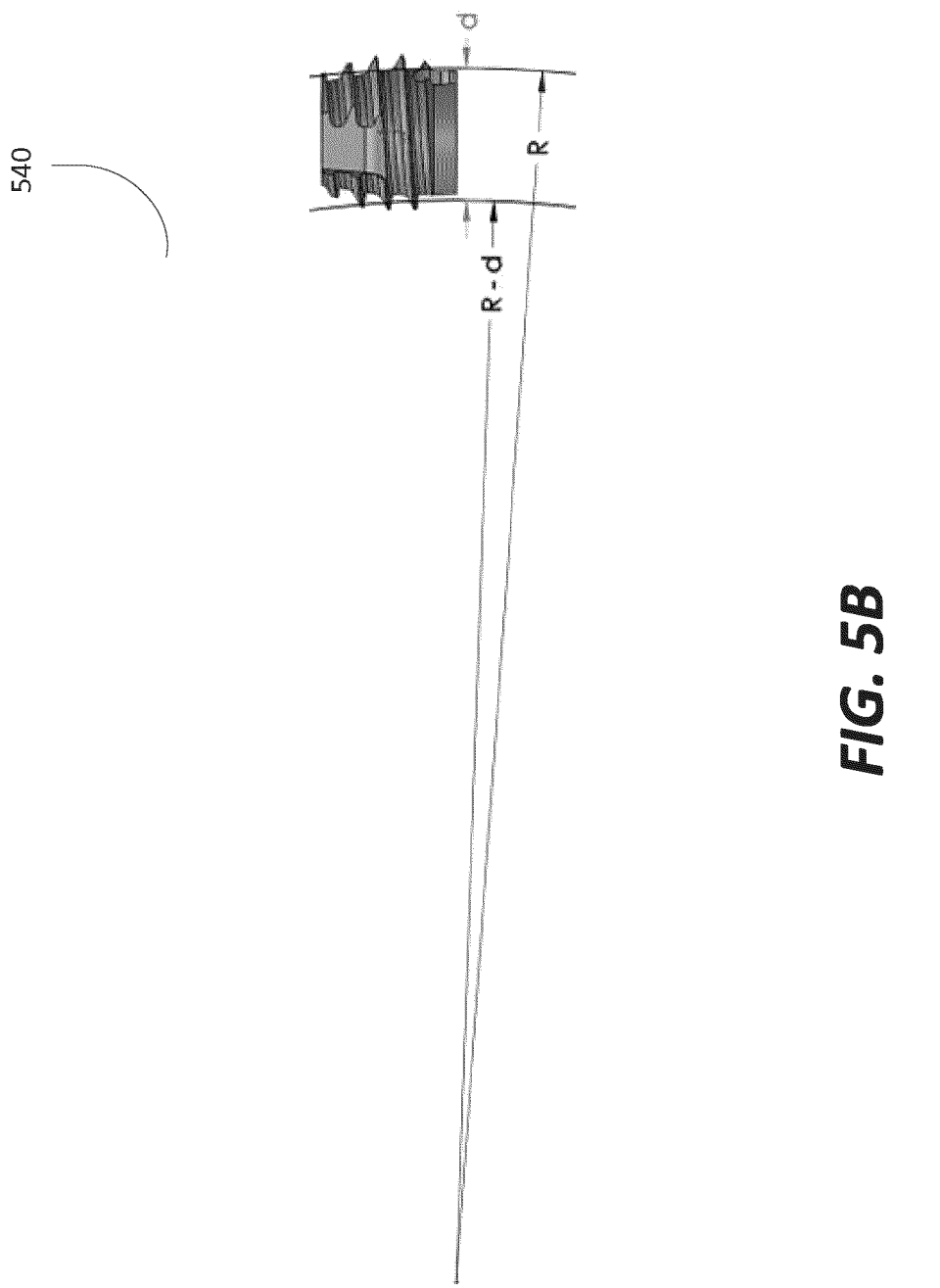
FIG. 5b depicts an alternative view of a distal interface in accordance with an illustrative embodiment.

In an embodiment, the distal interface 540 may be hollow or include a central bore 560 to receive a guide wire and/or a central tensioning member. The interior surface of the distal interface may also be the distal termination point for tensile fibers extending though the fixation device. In an embodiment, the fibers of the fixation device may be in a fixed position in the distal interface 540 during both the flexible state and the rigid state. The root face of the head of the distal interface 540 may have a tapered profile that can rotate through an arched lumen profile as illustrated in FIG. 5b.

Figure 6:
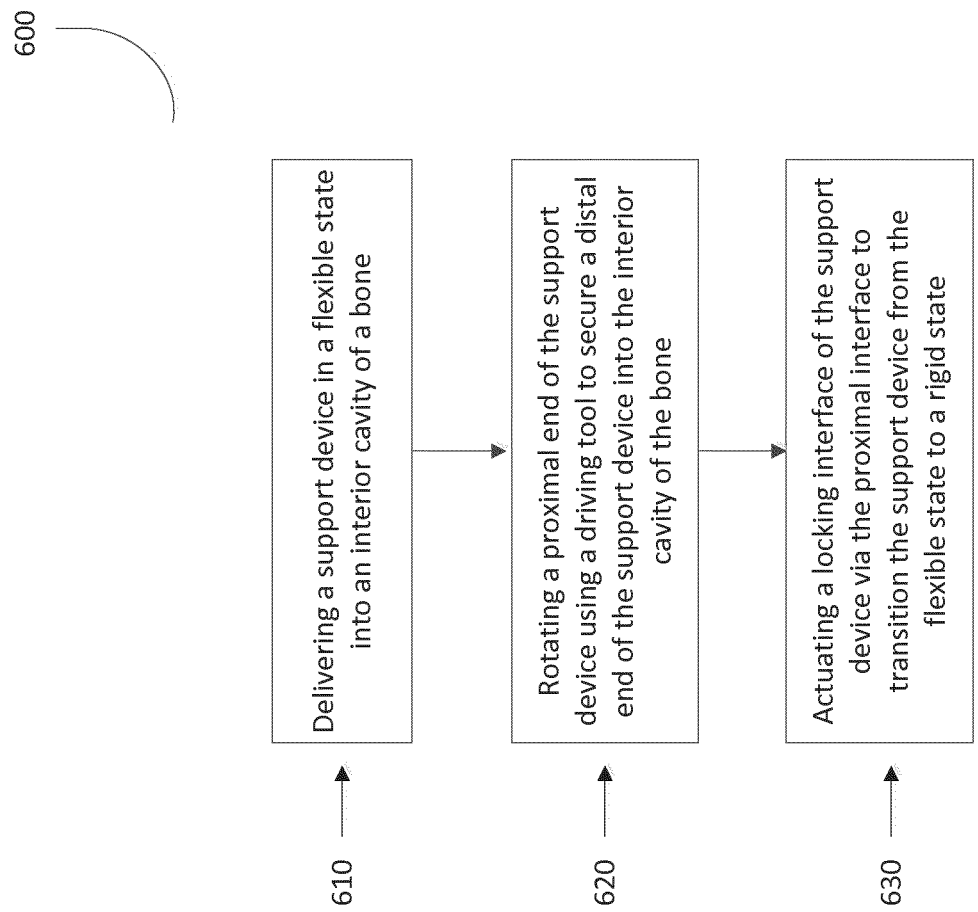
FIG. 6 depicts a flow diagram of a method for delivering a fixation device to a bone of a patient and converting the device from a flexible to rigid state in accordance with an illustrative embodiment.

Now referring to FIG. 6, a flow diagram of a method for delivering a fixation device to a bone of a patient is shown. As a brief overview, the method includes installing the fixation device in a flexible state into an interior cavity of the bone via an access point in the bone (step 610). The fixation device includes a flexible state and a rigid state. The method further includes rotating a proximal end of the fixation device using a driving tool to secure a distal end of the fixation device into the interior cavity of the bone (step 620). The method further includes actuating a locking interface of the fixation device via the proximal interface to convert the fixation device from a flexible state to a rigid state (step 630).

To deliver the fixation device to the bone of the patient, an access or pathway to the bone can be established through soft tissue surrounding the bone. In an embodiment, access to the bone is provided by a cannula placed through the soft tissue. Once the surface of the bone is reached, a hole or access point is made in the hard outer bone (i.e., cortical bone). The access point provides access to the interior bone surface or the cancellous bone region.

Next, a guide is placed though the cannula and into the interior cavity of the bone. In an embodiment, the guide is a low stiffness, bent tip steerable guide. The guide can be driven into the interior cavity of the bone under fluoroscopic observation. In an embodiment, the guide includes a sharp tip that is advanced and oriented toward the interior of the bone curvature, such that the tip does not dig into the exterior cortical wall. The steerable guide can follow the interior geometry of the bone to a desired or pre-determined depth past a fracture in the bone. The desired depth may be a point to allow a middle portion of a fixation device to be aligned with the fracture such that the distal end and proximal end of the fixation device receive and transfer similar or the same amounts of load between the fixation device and the bone once attached. In other embodiments, the desired depth may vary depending on the shape or geometry of the bone and where the fracture is in the bone.

When the guide has reached the desired depth, the guide may be replaced with a blunt tip guide wire. A flexible reamer can then be fed over the guide wire and through the interior cavity of the bone. The reamer increases the diameter of a bore through the interior cavity in the bone along the same path as the guide wire. The diameter may be increased to a point that allows the fixation device to be delivered and installed inside the bone.

Once the diameter of the bore has been increased to the appropriate size, the reamer is removed and exchanged with the fixation device. The fixation device can be inserted a flexible state into the interior cavity of the bone via the access point in the bone (step 610). The fixation device includes a flexible state and a rigid state. The fixation device can be delivered up to the exterior surface of the bone using the cannula.

The method further includes advancing the fixation device to a pre-determined point past a fracture in the bone. As stated above, the desired depth may be a point to allow a middle portion of a fixation device to be aligned with the fracture such that the distal end and proximal end of the fixation device receive and transfer similar or the same amounts of load between the fixation device and the bone once attached. In other embodiments, the desired depth may vary depending on the shape or geometry of the bone and where the fracture is in the bone.

The method further includes rotating a proximal end of the fixation device using a driving tool to secure a distal end of the fixation device into the interior cavity of the bone (step 620). When the fixation device reaches the exterior surface of the bone to be fixed, the fixation device can be rotated using a driving tool that interfaces with a proximal interface of the fixation device. The rotation of the proximal interface transmits torque through a locking interface and main body of the fixation device to the distal interface of the fixation device.

The distal interface may include a threaded exterior surface that pulls the distal interface and the fixation device into the bore of the interior cavity of the bone. The proximal interface is rotated until the proximal interface is adjacent to the exterior surface of the bone or flush with the access point created in the exterior surface of the bone. When the fixation device reaches the desired depth, the guide wire can be removed.

The method further includes actuating a locking interface of the fixation device via the proximal interface to convert the fixation device from a flexible state to a rigid state (step 630). In an embodiment, a driving tool is inserted into the proximal interface and engages an inner thread of the interior surface of the proximal interface. The inner thread provides a path to the locking interface through the proximal interface such that when the locking interface is rotated, the fixation device does not move relative to the bone, and can be converted from the flexible state to the rigid state.

In an embodiment, a locking screw of the locking interface is advanced through the locking interface to contact with a ram or interior body. In one embodiment, the ram rotates fibers in opposing directions causing the fibers to pinch against a locking face of the locking interface until they are clamped or restricted from moving. The restriction of the fibers restricts the movement and flexion of a main body of the fixation device. The main body includes a series of beads that are connected together and house a portion of the fibers. When the fibers are restricted in movement, the series of beads and fibers combine to form a rigid member. The degree of movement of the fibers may correspond to the degree of movement of the series of beads. For example, in the rigid state, the series of beads making up the main body are aligned relative to one another and restrict the motion of the fiber in the main body. In the rigid state, the movement of the fibers is restricted at the proximal end of the fixation device and the distal end of the device. Alternatively, in the flexible state, the movement of the fibers relative to one another is only restricted at the distal end of the fixation device.

In other embodiments, the interior body of the locking interface is advanced to a tapered section of the locking interface and applies pressure on the tensile fibers housed in the main body. The pressure pinches the fibers limiting and restricting their ability to move. The restriction from either the ram or the interior body movement causes the fibers to be offset relative to another fiber in the main body of the fixation device. The restriction causes the fibers to be offset relative to another fiber in the main body of the fixation device. In an embodiment, a series of beads making up the main body are aligned relative to one another and restricts the motion of the fibers in the main body. In the rigid state, the movement of the fibers is restricted at the proximal end of the fixation device and the distal end of the device. In the flexible state, the movement of the fibers relative to one another is only restricted at the distal end of the fixation device. The final rigid state of the fixation device will depend on the curvature or geometry of the bone to which the fixation device is attached. The fixation device can be tightened and loosened to accommodate the shape of the bone. In some embodiments, fibers can be added or removed from the fixation device prior to installation to increase or decrease the bend radius of the fixation device and strength of the device.

Figure 7A:
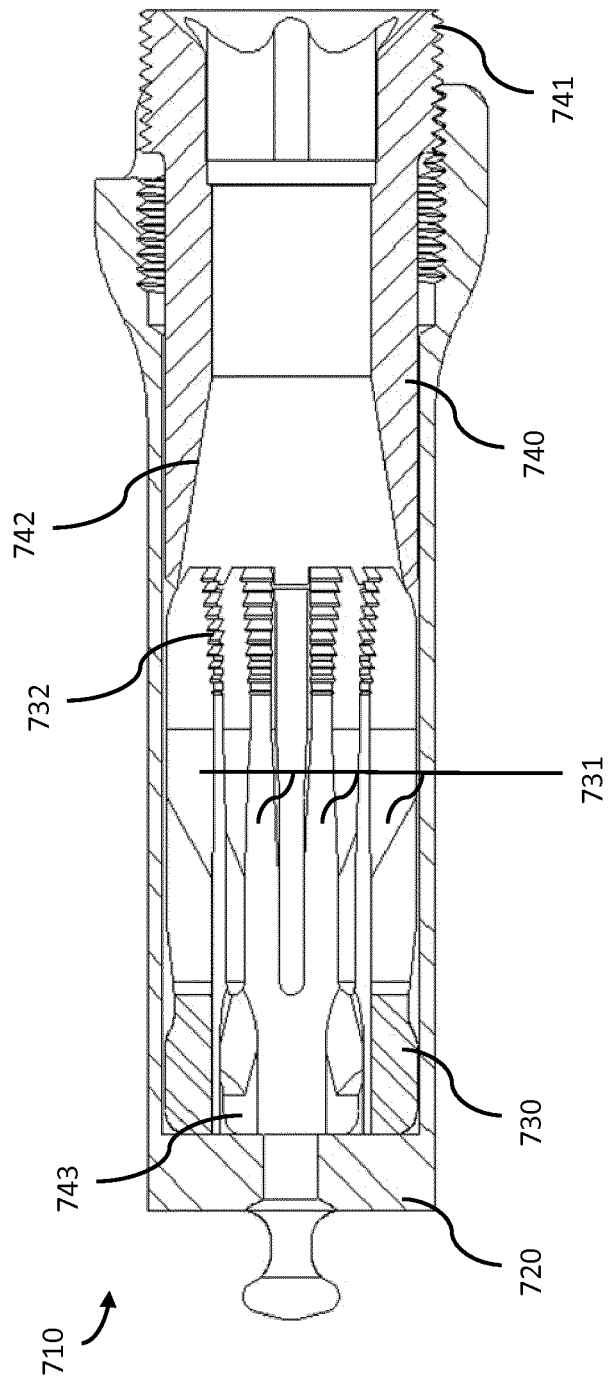
FIG. 7a depicts a locking interface in the unlocked position with a collet housing, collet, and collet lock in accordance with an illustrative embodiment.
Figure 7B:
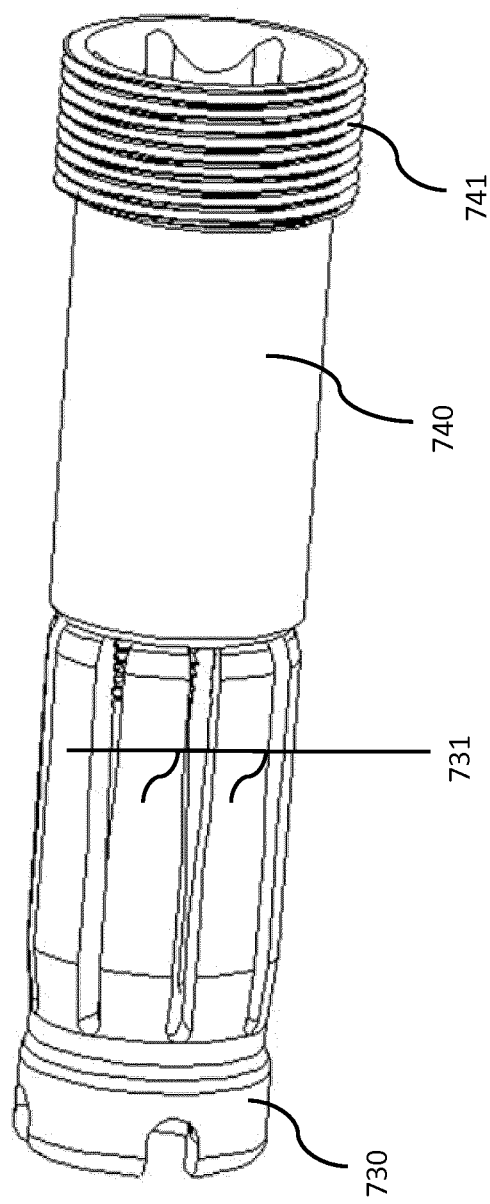
FIG. 7b depicts a collet and collet lock in accordance with an illustrative embodiment.

Now referring to FIG. 7*a*, a locking interface 710 is shown in the unlocked position. A collet housing 720 houses a collet 730 and a collet lock 740. The collet 730 has an ID in the open state of such size to permit all device cable and a guide wire to pass through. The proximal end of the collet 731, in the closed state reduces to a size sufficient to clamp 3 or more cables, without a guide wire in place. The collet lock 740 extends partially out of the collet housing 720 in the unlocked state, exposing threads 741. The exposed threads 740 of the collet lock 740 may be engaged with an insertion tool to handle the fixation device. The collet lock distal taper 742 interfaces with the collet arms 731, to squeeze teeth radially inward until such point that the cables of the device are gripped by the collet teeth 732. Collet Cable Reliefs 743 permit the cables to pass into the center of the collet 730, and prevent the collet from rotation within the collet housing 720. FIG. 7b depicts a collet 730 and collet lock 740 in accordance with an illustrative embodiment. The collet 730 and collet lock 740 of FIG. 7b may be similar to and used similar to the similarly numbered components of FIG. 7a. For example, the collet 730 includes the collet arms 731 and the collet lock 740 includes the threads 741.

In some embodiments, if the fixation device needs to removed, an access point must be made again through the soft tissue using the methods as described above. Once access to the fixation device is established, the device can be converted from the rigid state to the flexible state. The locking interface can be disengaged to allow flexion in the main body of the fixation device. In the flexible state, the device can be rotated out of the interior cavity of the bone using a driving tool interfaced with the proximal interface of the fixation device. The rotation can transmit torque through the main body of the device, up to the distal interface of the fixation device. In an embodiment, the torsional response of the main body sections will result in a section by section disengagement with any bone ingrowth, with the most proximal section breaking free of ingrowth first, then the second, then the 3rd, etc. When the entire main body of the fixation device has broken free of bone ingrowth, torque will be transmitted into the distal interface.

In an embodiment, the locking interface is rotated counter clockwise to retract the fixation device from the interior cavity of the bone. When driven counter clockwise, the threads on the head and exterior surface of the distal interface can push the fixation device out the bore of the bone until the distal end of the device reaches the exterior surface of the bone.

In other embodiments, to remove the fixation device a centering drill guide is applied over the proximal end of the fixation device. A thin walled flexible hole-saw matched with the outer diameter of the device may be used to cut away the bone around the device. The hole-saw is removed and the locking interface is disengaged to allow flexion in the main body of the fixation device. In the flexible state, the fixation device can be pulled from the bore of the bone.

In an embodiment, the four sections of the fixation device, the proximal interface 110, the locking interface 120, the main body 130, and the distal interface 140, are modular to a degree, such that the alternate embodiments described for each device section may be readily interchanged. All sections can be manufactured using standard machining, electrical discharge machining (EDM), and/or forging methods, for example, from 316LVM Stainless steel material. Other implantable materials may also be feasible for use, including but not limited to Ti Grade 23 6AI-4V extra low interstitial (ELI), and polyether ether ketone (PEEK). The use of the term "fiber" is inclusive of a multitude of cross sections including (but not limited to) round, rectangular, square, and bundles of any of the former.

One or more flow diagrams may have been used herein. The use of flow diagrams is not meant to be limiting with respect to the order of operations performed. The herein described subject matter sometimes illustrates different components contained within, or connected with, different other components. It is to be understood that such depicted architectures are merely illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A bone-fracture fixation device, comprising:
   a main body including a series of beads each including three or more fiber bores;
   three or more fibers each disposed in a respective one of the fiber bores; and
   a locking interface configurable to hold the fibers to cause the main body to be a rigid arched geometry, and configurable to release the fibers to cause the main body to be flexible.

2. The bone-fracture fixation device of claim 1 wherein each bead in the series of beads comprises a central bore and the three or more fiber bores are positioned around the central bore.

3. The bone-fracture fixation device of claim 1 wherein the three or more fibers run a length of the main body.

4. The bone-fracture fixation device of claim 1, further comprising:
   wherein the main body has an end; and
   wherein the three or more fibers are fixed adjacent the end of the main body.

5. The bone-fracture fixation device of claim 4, further comprising:
   another interface disposed adjacent to the end of the main body; and
   wherein the three or more fibers are fixed adjacent the other interface.

6. The bone-fracture fixation device of claim 4, further comprising:
   another interface disposed adjacent to the end of the main body; and
   wherein the three or more fibers are fixed at the other interface.

7. The bone-fracture fixation device of claim 1 wherein the main body is able to flex in one or more axes of motion in response to the locking interface being configured to cause the main body to be flexible.

8. The bone-fracture fixation device of claim 1, further comprising:
   wherein the main body has an end; and
   wherein the locking interface is configurable to hold the three or more fibers in a fixed position adjacent the end to cause the main body to be a rigid arched geometry.

9. The bone-fracture fixation device of claim 1, further comprising:
   wherein the main body has an end; and
   wherein the locking interface is disposed adjacent the end and is configurable to hold the three or more fibers in a fixed position to cause the main body to be a rigid arched geometry.

10. The bone-fracture fixation device of claim 1 wherein each bead comprises a pair of lobes positioned at opposing ends of the respective bead and extending perpendicular from a first surface of the respective bead.

11. The bone-fracture fixation device of claim 10 wherein:
    each bead comprises a pair of sockets formed into a second surface of the respective bead and positioned at opposing ends of the respective bead; and
    wherein the pair of sockets of each bead receives the pair of lobes of a respective preceding bead in the series of beads to form the series of beads.

12. The bone-fracture fixation device of claim 10 wherein:
    each bead comprises a pair of sockets formed into a second surface of the respective bead and positioned at opposing ends of the respective bead; and
    wherein the pair of lobes of each bead is disposed within a pair of sockets of a respective subsequent bead in the series of beads.

13. The bone-fracture fixation device of claim 10 wherein the first surface of each bead is configured to limit a bead-to-bead angulation in the series of beads to a predetermined angle corresponding to a minimum bend radius of the main body.

14. The bone-fracture fixation device of claim 1, further comprising:
    wherein the main body includes an end; and
    another interface disposed adjacent the end and including a threaded outer surface configured to anchor the main body to an interior cavity of a bone while the main body device is installed in the interior cavity of the bone.

15. The bone-fracture fixation device of claim 14 wherein the other interface comprises a central bore configured to receive a guide wire.

16. The bone-fracture fixation device of claim 1 wherein the locking interface is configured to transition from one of holding the fibers and releasing the fibers to the other of holding the fibers and releasing the fibers without changing a shape of the main body.

17. The bone-fracture fixation device of claim 1 wherein the main body is configurable to have a shape that is independent of whether the main body is flexible or rigid.

18. The bone-fracture fixation device of claim 1 wherein at least one of the three or more fibers is configured to support, at least partially, a load imposed on the main body while the main body is a rigid arched geometry.

19. The bone-fracture fixation device of claim 1 wherein the locking interface is configured to hold the three or more fibers by restricting movement of each of the three or more fibers relative to the other fibers in a direction along a longitudinal axis of the main body.

20. A bone-fracture fixation device, comprising:
    a main body including a series of beads each including three or more respective fiber bores and at least one respective surface configured to set a minimum bend radius of the main body by limiting a bead-to-bead angulation;

three or more fibers each disposed in a respective one of the fiber bores of each of the beads; and a locking interface configurable to hold the fibers to cause the main body to be a rigid arch having a radius that is greater than or equal to the minimum bend radius, and configurable to release the fibers to cause the main body to be flexible.

\* \* \* \* \*

UNITED STATES PATENT AND TRADEMARK OFFICE
CERTIFICATE OF CORRECTION

PATENT NO. : 10,973,559 B2
APPLICATION NO. : 16/384758
DATED : April 13, 2021
INVENTOR(S) : Edward Scott Harshman, Steven Charles Dimmer and David Thomas Stinson Page 1 of 1

It is certified that error appears in the above-identified patent and that said Letters Patent is hereby corrected as shown below:

On the Title Page

On Page 4, item (56) Under Other Publications, Column 1, Line 38 from the top, please replace "Adults fith Edition" with --Adults 6th Edition--

On Page 4, item (56) Under Other Publications, Column 2, Line 6 from the top, please replace "pp. 14" with --Page (s) 1-4--

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*